United States Patent [19]

Muchwoski et al.

[11] Patent Number: 4,867,915

[45] Date of Patent: Sep. 19, 1989

[54] 16-SUBSTITUTED POLYUNSATURATED HEXADECANOIC FATTY ACIDS

[75] Inventors: Joseph M. Muchwoski, Sunnyvale, Calif.; Angel Guzman, Mexico City, Mexico

[73] Assignee: Syntex (U.S.A.) Inc., Palo Alto, Calif.

[21] Appl. No.: 866,037

[22] Filed: May 21, 1986

[51] Int. Cl.$^4$ ............................................. C07C 61/29
[52] U.S. Cl. .................................. 260/399; 260/402; 260/404; 260/408; 260/410.9 R; 260/413; 514/522; 514/532; 514/543; 514/822; 514/825; 514/826; 514/886
[58] Field of Search ................ 260/404, 410.9 R, 408, 260/413, 402, 399; 514/522, 532, 543, 822, 825, 826, 886

[56] References Cited

U.S. PATENT DOCUMENTS

| | | | |
|---|---|---|---|
| 3,862,972 | 1/1975 | Heslinga et al. | 260/410.9 R |
| 3,972,907 | 8/1976 | Baran et al. | 260/410.9 R |
| 4,054,589 | 10/1977 | Bollag et al. | 260/408 |

*Primary Examiner*—Warren B. Lone
*Attorney, Agent, or Firm*—Brian Lewis; Tom M. Moran; Alan M. Krubiner

[57] ABSTRACT

Sixteen carbon atom carboxylic acids having 16-phenoxy or 16-phenylthio substituents, and 0, 1, or 4 triple bonds, methods of preparing them, and pharmaceutical preparations containing them. These compounds are useful as lipoxygenase inhibitors.

35 Claims, No Drawings

16-SUBSTITUTED POLYUNSATURATED HEXADECANOIC FATTY ACIDS

BACKGROUND OF THE INVENTION

1. Field of the Invention

This invention relates to fatty acid derivatives, particularly sixteen carbon atom carboxylic acids which are substituted by a 16-phenoxy or a 16-phenylthio substituent. This invention also relates to the use of these compounds for the treatment of diseases characterized by inflammation, to pharmaceutical compositions containing these derivatives and to processes for preparing these derivatives.

2. Related Disclosures

Arachidonic acid is a naturally occurring polyunsaturated fatty acid, also known as eicosa 5(Z), 8(Z), 11(Z), 14(Z)-tetraenoic acid. It was first isolated from the liver and has been synthesised by several methods, see, for example, A. I. Raschlind et al, *J. Org. Chem.*, 26, 2688, (1961), and J. M. Osbond et al, *Chem. and Ind.* (*London*), 1959, 1288. Arachidonic acid is converted to a variety of naturally occuring compounds in the mammalian metabolism, including, for example, prostaglandins, thromboxanes, and leukotrienes. All of the major metabolic products of arachidonic acid are known to be involved in various disease states. Among the enzymes involved in this complex biochemical process, known as the "arachidonic acid cascade", are fatty acid cyclooxygenase and lipoxygenase. A more complete discussion of the arachidonic acid cascade can be found at *Chem. and Eng. News*, Aug. 16, 1982, 30–44. Certain arachidonic acid derivatives have been prepared. These include eicosa-5,8,11,14-tetraynoic acid, disclosed by J. M. Osbond et al, *J. Chem. Soc.*, 2779 (1961); eicosa-8(Z),11(Z),14(Z)-trien-5-ynoic acid, described by H. Heslinga et al. in *Recueil*, 94, 262 (1975); nonadeca-5(Z),8(Z),11(Z),14(Z)-trien-5-ynoic acid described by R. K. Beerthuis et al. in *Recueil*, 87, 461 (1968); and octadeca-5,8,11,14-tetraynoic acid described by R. K. Beerthuis et al. in *Recueil*, 90, 943 (1971).

A new family of sixteen carbon atom carboxlic acid derivatives related to arachidonic acid have now been discovered. These compounds inhibit lipoxygenase and are useful for treating disease states characterized by inflammation.

SUMMARY OF THE INVENTION

One aspect of this invention is a compound of the formula

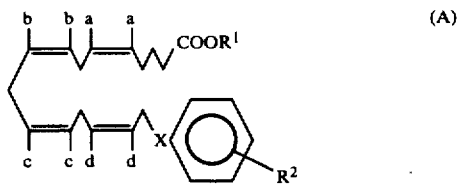

(A)

wherein:
X is O or S;
R¹ is hydrogen, lower alkyl or a pharmaceutically acceptable cation;
R² is hydrogen, lower alkyl, lower alkoxy, halo cyano, trifluoromethyl, lower alkylthio, lower alkylsulfinyl or lower alkylsulfonyl, provided that when X is S R² cannot be alkylsulfinyl or alkylsulfonyl;
and each pair of a—a, b—b, c—c, and d—d are independently hydrogens or a covalent bond.

Another aspect of this invention is a pharmaceutical composition that comprises a compound of formula (A) in combination with a pharmaceutically acceptable excipient.

Still another aspect of this invention is the treatment of a mammal having a disease state characterized by inflammation which method comprises administering a therapeutically effective amount of a compound of formula (A) to the mammal.

Still another aspect of this invention is the preparation of a compound of formula (A).

DETAILED DESCRIPTION OF THE INVENTION

Definitions

As used in this specification the term "alkyl" means a branched or unbranched saturated hydrocarbon chain containing the number of carbon atoms indicated, e.g., methyl, ethyl, n-propyl, isopropyl and n-butyl.

As used in this specification the term "alkoxy" means the group —OR wherein R is alkyl as defined above. Examples include methoxy, ethoxy, n-propoxy, n-butoxy, tert-butoxy and the like.

The term "alkylthio" refers to the group —SR in which R is alkyl as defined above.

The terms "alkylsulfinyl" and "alkylsulfonyl" refer to the group —S(O)$_n$—R in which n is the integer 1 or 2, respectively, and R is alkyl as previously defined.

As used in this specification the term "lower" as used herein, modifies alkyl, alkoxy, alkylthio, alkylsulfinyl, and alkylsulfonyl and refers to those radicals having four carbon atoms or less.

As used in this specification the term "halo" means fluoro, chloro, bromo, or iodo.

As used in this specification the term "optional" or "optionally" means that the subsequently described event or circumstance may or may not occur, and that the description includes instances where said event or circumstance occurs and instances in which it does not. "Optionally followed by converting the free base to the acid addition salt" means that said conversion may or may not be carried out in order for the process described to fall within the invention, and the invention includes those processes wherein the acid is converted to the salt and those processes in which it is not.

As used in this specification the term "optionally substituted phenyl" means a phenyl moiety, which may or may not be substituted, as indicated in the previous paragraph, with substituents selected from the group consisting of halo, alkyl of one to six carbon atoms, or alkoxy of one to six carbon atoms, hydroxy, and trifluoromethyl.

When optical isomers are possible, for example with asymmetric branched alkyl groups, each isomer, the racemic mixture and mixtures that are not racemic fall within the scope of the claims.

As used in this specification the term "treatment" means any treatment of a disease in a mammal, and includes:

(i) preventing the disease, that is, causing the clinical symptoms of the disease not to develop;

(ii) inhibiting the disease, that is, arresting the development of clinical symptoms; or (iii) relieving the disease, that is, causing regression of of clinical symptoms.

The term "pharmaceutically acceptable cation" refers to a positively charged radical from pharmaceutically acceptable non-toxic bases, including inorganic and organic bases.

Inorganic cations include sodium, potassium, lithium, ammonium, calcium, magnesium, ferrous, zinc, copper, manganous, aluminum, ferric, and manganic salts, and the like. Particularly preferred are the ammonium, potassium, sodium, calcium and magnesium cations.

Organic cations include those derived from pharmaceutically acceptable organic non-toxic bases and such as primary, secondary and tertiary amines, substituted amines including naturally occurring substituted amines, cyclic amines and basic ion exchange resins. Examples include isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, N-methylglucamine, theobromine, purines, piperazine, piperidine, N-ethylpiperidine, and polyamine resins, and the like. Particularly preferred organic non-toxic bases are isopropylamine, diethylamine, ethanolamine, piperidine, tromethamine, choline and caffeine.

Presently Preferred Embodiments

Preferred compounds of this invention include compounds represented by the formulae:

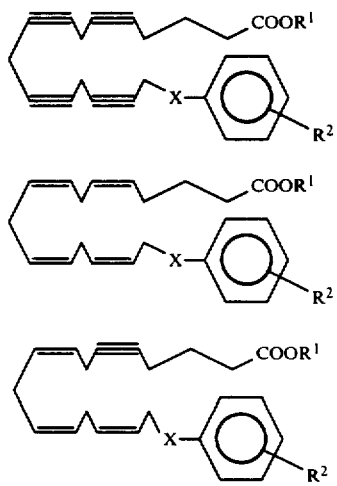

wherein $R^1$, $R^2$ and X have the above-indicated meaning. The double bonds in compounds represented by formulas (C) and (D) are in cis (Z) configuration.

Representative compounds of Formula A include those with the following substitutions:

| | X | $R^1$ | $R^2$ | a—a | b—b | c—c | d—d |
|---|---|---|---|---|---|---|---|
| 1 | O | H | —H | H | H | H | H |
| 2 | O | H | —H | cb | cb | cb | cb |
| 3 | O | H | -3-CH$_3$ | H | H | H | H |
| 4 | O | H | -3-CH$_3$ | cb | cb | cb | cb |
| 5 | O | H | -4-CH$_3$ | H | H | H | H |
| 6 | O | H | -4-CH$_3$ | cb | cb | cb | cb |
| 7 | O | H | -3-Cl | H | H | H | H |
| 8 | O | H | -3-Cl | cb | cb | cb | cb |
| 9 | S | H | —H | H | H | H | H |
| 10 | S | H | —H | cb | cb | cb | cb |
| 11 | O | H | —H | cb | H | H | H |

-continued

| | X | $R^1$ | $R^2$ | a—a | b—b | c—c | d—d |
|---|---|---|---|---|---|---|---|
| 12 | O | H | -4-SCH$_3$ | cb | cb | cb | cb |
| 13 | O | H | -4-S(O)$_2$CH$_3$ | cb | cb | cb | cb |
| 14 | O | H | -4-S(O)CH$_3$ | H | H | H | H |
| 15 | O | H | -4-S(O)$_2$CH$_3$ | H | H | H | H |
| 16 | O | H | —CH$_3$ | cb | H | H | H | where H represents one hydrogen in the definition of $R^1$ and $R^2$ and H represents two hydrogens in the definition of a—a, b—b, c—c, d—d and cb represents a covalent bond.

Utility and Methods of Administration

The compounds of this invention are useful for treating mammals having a variety of disease states characterized by overproduction of the products of the lipoxygenase metabolism of arachidonic acid. Disease states that may be treated include inflammatory diseases including rheumatoid arthritis, inflammatory bubble disease; psoriasis; various cardiovascular syndromes, particularly those characterised by inappropriate clotting of the blood, such as thrombosis, and the like; and hypersensitivity diseases, such as asthma.

Generally, the diseases characterized by overproduction of the products of the lipoxygenase metabolism of arachidonic acid are found in mammals including domestic commercial animals such as horses, cattle, sheep and pigs; domestic house animals such as dogs, cats and the like; and particularly humans.

In vitro lipoxygenase inhibiting activity of the compounds of this invention are determined by the standard Human Polymorphonuclear Leukocytes assay. This assay is a modification of that described by O. Radmark, C. Malmasten, and B. Samuelsson in *Febs Letter*, 110, 213–215. In vivo lipoxygenase inhibiting activity of the compounds of this invention are determined by the croton oil induced rat ear inflammation assay as described by G. Tonelli, L. Thidould, and I. Ringler in *Endocrinology*, 77, 625–634 (1965).

The compounds of this invention are administered at a therapeutically effective dosage, i.e. a dosage sufficient to inhibit the activity of lipoxygenase. Administration of the active compounds and salts described herein can be via any of the accepted modes of administration for agents which are antiinflammatory agents. Depending on the specific disease state, administration can be systemic, via parenteral, oral, intravenous, or nasal routes; or topical.

The compounds of this invention are generally administered as a pharmaceutical composition which comprises a pharmaceutical excipient in combination with a compound of formula (A). Depending on the type of composition, the compound of formula (A) is present in an amount ranging from about 0.5 wt % to 95.0 wt % with an excipient in the range of about 99.5 wt % to 5.0 wt %.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 18th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formualtions and the like. Such compositions may contain 10%-95% active ingredient, preferably 25-70%.

For systemic administration via suppository, traditional binders and carriers include, e.g. polyalkylene glycols or triglycerides. Such suppositories may be formed from mixtures containing active ingredient in the range of 0.5%-10%; preferably 1-2%.

Process of Preparing the Compounds of the Invention

The novel polyunsaturated fatty acids of formulas (B) and (C) in which $R^1 = H$, Me or Et are prepared by a method illustrated by REACTION SCHEME I:

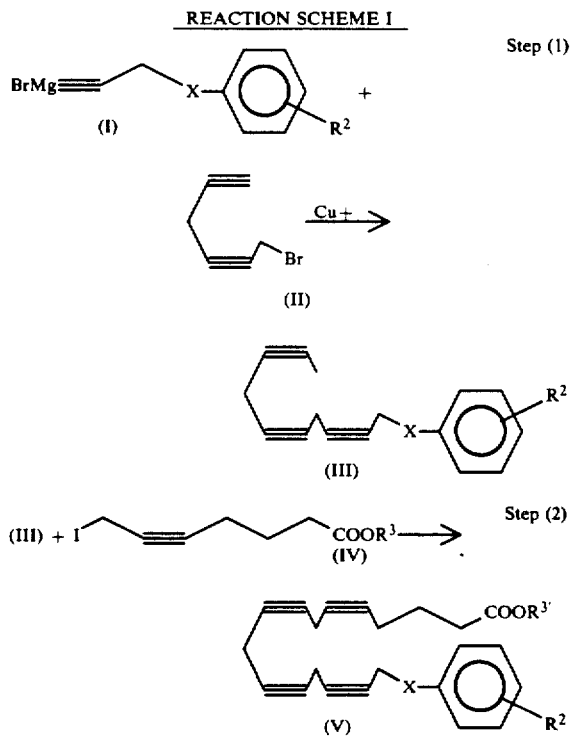

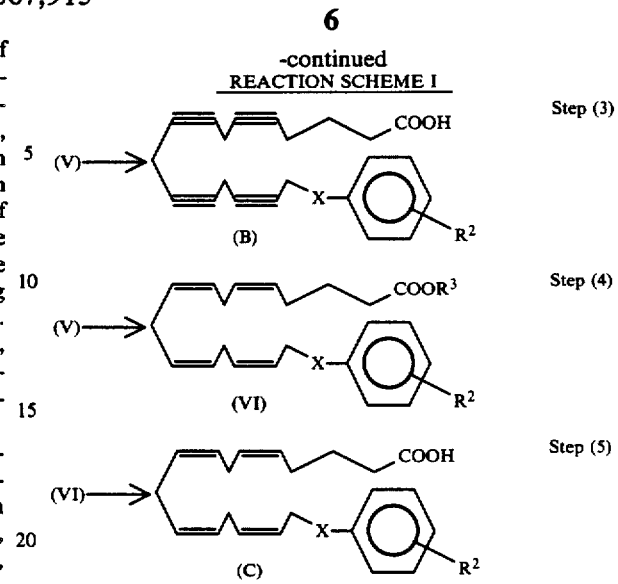

In REACTION SCHEME I X and $R^2$ are as defined in the summary of the invention above, $R^3$ is methyl or ethyl and $R^{3'}$ is methyl, ethyl or a mixture thereof.

STEP (1) of the above-depicted process involves the coupling of the Grignard reagent of a phenylpropargyl ether or a phenylpropargyl thioether (I) with 1-bromo-2,5-hexadiyne (II) [R. I. Fryer et al, *J. Org. Chem.*, 40, 348 (1975)] in the presence of cuprous ion, to produce the corresponding 1,4,7-nonatriyne of formula (III).

The phenylpropargyl ethers and phenylpropargyl thioethers used as starting materials for the complex (I) are known compounds, see for example, G. Pourcelot et al, *Bull. Soc. Chim.* (1966), 3016; I. Iway et al, *Chem. Pharm. Bull.* (*Jap*), 11, 1042 (1963) and *Chem. Abst.*, 82, 155636 d (1975)] or can be prepared by the methods described therein. Such methods involve conversion of the appropriate phenol or thiophenol, which may be optionally substituted at o-, m- or p-positions, with appropriate $R^2$ substituents, into the sodium phenolate or thiophenolate by conventional treatment with alkali metal alkoxides, hydroxides or carbonates in, for example, anhydrous ethanol or acetone as solvent, followed by condensation with propargyl bromide at reflux temperature for about 10 to 15 hours to form a phenylpropargyl ether or a phenylpropargyl thioether.

The reaction of STEP (1) is conducted under anhydrous conditions, in an ether solvent, e.g., tetrahydrofuran, diethylether, 1,2-dimethoxyethane, and the like, or mixtures thereof and under an inert atmosphere, at a temperature of between $-20°$ C. to $50°$ C., for a period of time sufficient to complete the reaction, typically on the order of 3 to 6 hours. Initially, a solution of phenylporpargyl ether or a phenylpropargyl thioether, in an ethereal solvent, using preferably anhydrous tetrahydrofuran as solvent, is treated with 1-1.1 molar equivalents of a Grignard reagent such as a 3-4N ethereal solution of ethylmagnesium bromide, preferably at a temperature of between $-10°$ to $10°$ C., under nitrogen or argon atmosphere for about 1 hour, to form the Grignard reagent, which is immediately coupled with 1-bromo-2,5-hexadiyne in the same reaction medium, in the presence of catalytic amounts of a cuprous salt such as cuprous cyanide, cuprous chloride, cuprous bromide or cuprous iodide. The preferred source of cuprous ion in this reaction is cuprous cyanide.

This coupling is preferably conducted at a temperature of between −10° to 40° C. It is particularly preferred to start the reaction at −10° to 0° C., and allow the temperature to gradually rise to ambient or slightly higher once the 2,5-hexadiyne (II) reagent has been added. The course of the reaction is monitored by thin layer chromatography (TLC) analysis, and it is substantially complete within 3 to 6 hours, depending upon the starting material and temperature at which it is carried out.

Although this coupling reaction may be conducted using varying proportions of reactants, it is preferred to use a 1:1 to 2:1 molar ratio of starting material (I) to 1-bromo-2,5-hexadiyne (II). After completion, the reaction is treated with a dilute acid, preferably with a dilute ice-cold aqueous mineral acid such as sulfuric acid or hydrochloric acid, and the product isolated from the reaction mixture by the usual techniques for this type of reaction, for example, extraction with a low-boiling solvent immiscible with water, such as diethyl ether or methylene chloride, followed by repeated washings of the extract with tetra-sodium ethylenediaminetetraacetic acid (EDTA) to remove copper salts and purification of the 1,4,7-nonatriyne compound (III) by chromatography.

In STEP (2) compound (III) is coupled with the methyl or ethyl ether of a 7-halo-5-heptynoic acid, particularly 7-iodo-5-heptynoic acid (IV), using essentially the same reaction conditions described in STEP (1) in detail. The formation of the Grignard reagent of (III) is followed by reaction with the iodoheptynoic acid ester in the presence of cuprous ion, producing the corresponding ester of a 16-phenoxy- or 16-(thiophenyl)hexadeca-5,8,11,14-tetraynoic acid (V). It is noteworthy that when 7-iodo-5-heptynoic acid methyl ester is used, trans-esterification with the Grignard reagent may occur, thus obtaining a mixture of the methyl and ethyl esters. If desired, the individual esters can be separated by chromatographic techniques.

This second coupling is preferably conducted at a temperature of between 20° to 50° C., preferably at about 40° C. when X is oxo, or room temperature when X is thio, for a period of time of between 3 to 6 hours. Stoichiometric amounts of reactants are used. However, this is not critical as larger proportions of any of them are also practical.

The methyl and ethyl esters of 7-iodo-5-heptynoic acid used in the above reaction are obtained from the tetrahydropyranyl ether of 7-hydroxy-5-heptynoic acid (U.S. Pat. No. 3,801,623). The tetrahydropyranyloxy function is split off with acid treatment. The carboxylic acid function is esterfied with methanol or ethanol in the presence of a strong acid by Fisher's esterification method. The 7-hydroxyl group is then esterified with methanesulfonyl chloride, preferably in methylene chloride solution, in the presence of a tertiary amine such as triethylamine. Finally, the crude mesylate is reacted with an excess of sodium iodide in aqueous dimethylsulfoxide solution. The reaction conditions are those conventionally used in the art.

In STEP (3) the compounds of formula (V) (methyl or ethyl esters or a mixture thereof) are enzymatically hydrolyzed with a lipase, using particularly Sigma Lipase, Type VII from Candida cylindracea. The lipase is used in a buffer solution of disodium hydrogen phosphate and potassium dihydrogen phosphate, at an almost neutral pH. Under these conditions the corresponding tetraynoic acid (B) is obtained. This enzymatic hydrolysis is preferably carried out at a pH ∼6.7, under vigorous stirring, at a temperature of between 20° to about 35° C., preferably at room temperature, for a period of time ranging from about 30 minutes to about 24 hours, depending on which ester is to be hydrolyzed. Other buffers having a pH 6.7 to 7.4 are also practical. A large excess of lipase, i.e., from 10 to 30 fold by weight of starting ester is employed, depending also on which ester is to be hydrolyzed. The course of the reaction is followed by TLC analysis. It is convenient to work the reaction mixture up under acidic conditions by adding, for example, a saturated solution of oxalic acid followed by extraction with a solvent immiscible with water such as ethyl acetate, methylene chloride, diethyl ether and the like, and purification of the free acid B by chromatographic techniques.

In STEP (4) the tetraynoic acid ester (V) is reduced to the corresponding all cis-tetraenoic compounds (VI) by catalytic hydrogenation in a suitable solvent or mixture of solvents, in the presence of Lindlar's catalyst partially deactivated by quinoline. In the preferred embodiments, this hydrogenation is conducted using from 10 to 20% by weight of both the catalyst and quinoline, in a 1:1 mixture of methanol-ethyl acetate as solvent, at ambient temperature and atmospheric pressure, until the calculated amount (4 moles) of hydrogen is consumed. Larger proportions of catalyst, i.e., up to 50% by weight of starting materials are sometimes required in the hydrogenation of the thio compounds.

The methyl or ethyl ester group, $R^3$, is then eliminated by alkaline treatment, i.e., by treatement with an alkali metal hydroxide or alkali metal carbonate such as sodium hydroxide, potassium hydroxide, lithium hydroxide, sodium carbonate, and potassium carbonate, and the like. An aqeous solution of alkyl lower alcohol, with an optional amount of tetrahydrofuran, using particularly a 0.5N alkali metal hydroxide is reacted to produce the corresponding 16-substituted-tetraenoic acid of formula (C). This hydrolysis reaction is preferably conducted at room temperature for a period of time of the order of between 3 to 60 hours, depending upon the starting compound. Upon selective oxidation of compounds of formulas (V) and (VI) in which $R^2$ is lower-alkylthio and (X) is O with potassium hydrogen persulfate the corresponding alkylsulfinyl or alkylsulfonyl derivatives are obtained, depending upon the conditions in which the oxidation takes place. Thus, the alkylsulfinyl compounds are obtained when using molar ratios of oxidizing agent and alkylthio compound, conducting the reaction between −10° C. to 10° C., for a short period of time, of between 3 to 20 minutes. In the preferred embodiments, this oxidation is effected at 0° for about 5 minutes.

The alkylsulfonyl derivatives are produced when between 1.5 to 2 molar equivalents of potassium hydrogen persulfate are employed. In this case, the oxidation is carried out at temperature between 0° C. to 30° C., preferably at room temperature for about 1 to 3 hours. Suitable solvents are those miscible with water, for example, lower aliphatic alcohols, such as methanol, ethanol, propanol, and the like, ethers, such as tetrahydrofuran, dioxane, and the like, or mixtures thereof. Good results are obtained when using tetrahydrofuran-methanol mixtures as solvent. Alternatively, this oxidation can be carried out with sodium metaperiodate. These sulfinyl and sulfonyl derivatives are converted into the free acids that correspond to formulas (V) and (VI), $R^2$ is $S(O)_n$—R and X is O, by the methods previously described for the enzymatic hydrolysis of the alkyl ester group in the case of the tetraynoic compounds and by alkaline treatment for the tetraenoic derivatives.

The compound of formula (D) in which $R^1$ is hydrogen or methyl are prepared by the method illustrated by REACTION SCHEME II:

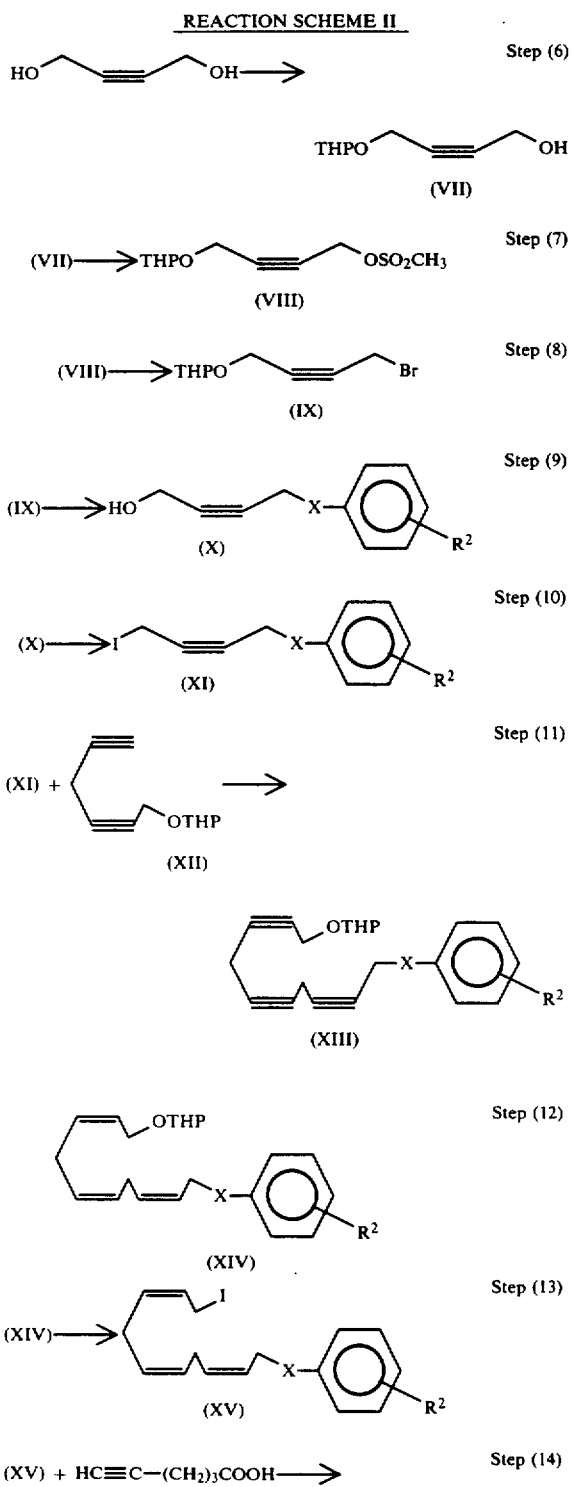

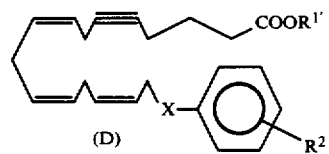

In REACTION SCHEME II, X and $R^2$ are as defined in the summary of the invention above, $R^4$ is hydrogen or tetrahydropyranyl and $R^{1'}$ is hydrogen or methyl.

In STEP (6) the starting material 2-butyne-1,4-diol, a commercially available compound is conventionally etherified with dihydropyran in the presence of an acid catalyst, such as p-toluenesulfonic acid, in a suitable inert solvent, e.g., tetrahydrofuran, to produce the monotetrahydropyranyl ether (VII) and a small amount of the bis-tetrahydropyranyl ether. The latter compound can be selectively hydrolyzed to the monoetherified derivative by reacting it with pyridinium p-tolenensulfonate in ethanol solution, at a temperature of between 40° to 60° C., preferably at about 55° C., for between 1 to 3 hours.

In STEP (7) the monotetrahydropyranyl ether is readily converted into the mesylate (VIII) by reaction with methanesulfonyl chloride in the presence of a tertiary amine, such as triethylamine, in an inert organic solvent, using preferably methylene chloride as solvent. The reaction is carried out at between −10° to 10° C., preferably at 0° C., for between 20 minutes to 1 hour. Between 1.1 to 2 molar equivalents of methanesulfonyl chloride and triethylamine, preferably about 1.5 molar equivalents of each reagent, is used per mole of starting material.

In STEP (8) the crude mesylate (VIII) is then treated with an excess of between 3 to 8 molar equivalents of an alkali metal bromide, preferably 5 molar equivalents of lithium bromide in acetone solution, at between 20° to 50° C. for a period of time between 30 minutes to 3 hours. 1-Bromobut-2-yn-4-ol tetrahydropyranyl ether, compound (IX), is produced by this reaction.

In STEP (9) compound (IX) is condensed with phenol, thiophenol or an optionally substituted derivative. Compound (X), the corresponding phenoxy- or phenylthio derivatives are thus obtained. The condensation is effected via formation of the sodium phenolate or thiphenolate by, for example, reacting first stoichiometric amounts of a phenol with sodium hydroxide or a thiophenol with sodium ethoxide, in an anhydrous lower alkyl alcohol, preferably ethanol, at reflux temperature, and then adding the bromo compound (IX). Preferably, the condensation takes place at reflux temperature, in between 1 to about 4 hours. Although the reaction consumes the reactants in molar basis, it is preferred to use 2 molar equivalents of the phenol or thiophenol per mole of the bromo compound.

Upon conventional hydrolysis of the tetrahydropyranyloxy moiety, using preferably, for example, pyridinium p-toluenesulfonate in ethanol solution, at a temperature between room temperature and reflux, for a period of time of between 1 to 10 hours, the corresponding 4-substituted but-2-yn-1-ol Compound (X). This hydrolysis works best at about 55° C. for 2 to 4 hours.

In STEP (10) the hydroxyl group is then esterified with methanesulfonyl chloride in methylene chloride solution and in the presence of triethylamine. This reaction is essentially as described herein for STEP (8). The crude mesylate is reacted with an excess of sodium iodide in the presence of sodium bicarbonate, to produce the corresponding 1-iodo-4-substituted but-2-yne, Compound XI. Between 2 to 5 molar equivalents of sodium iodide is used, preferably 3 molar equivalents with 1 molar equivalent of sodium bicarbonate. Preferably, the reaction is conducted in acetone solution, at room temperature for between 20 minutes to 2 hours. In general, it is complete within about 1 hour.

In STEP (11) compound (XI) is then coupled with the tetrahydropyranyl ether of hexa-2,5-diyn-1-ol (XII) [(D. Van der Steen et al, *Recueil*, 82, 1015 (1963)] via formation of the Grignard derivative, in the presence of cuprous ion, to produce the corresponding 10-substituted-deca-2,5,8-triyn-1-ol tetrahydropyranyl ether, Compound (XIII). The reaction conditions are essentially the same as those described in detail for STEP (1), however, the preferred catalyst is cuprous chloride. In addition, there is preferably employed 2 molar equivalents of reagent per mol of iodo compound.

In STEP (12) compound (XIII) is then catalytically hydrogenated in an inert solvent or mixture of solvents, in the presence of Lindlar's catalyst partially deactivated by quinoline, at ambient temperature and atmospheric pressure, until absorption of 3 moles of hydrogen, to produce the corresponding all cis decatriene derivative, Compound (XIV).

In STEP (13) the tetrahydropyranyloxy function of compound (XIV) is hydrolyzed, followed by esterification of the hydroxyl group with mesyl chloride in methylene chloride-triethylamine and treatment of the mesylate with sodium iodide in the presence of sodium bicarbonate in acetone solution, as previously described. 1-Iodo-10-substituted deca-2(Z),5(Z),8(Z)-triene, compound (XV) is obtained.

In STEP (14) compound (XV) is then coupled with 5-hexynoic acid, to produce the corresponding 16-substituted-hexadeca-8(Z),11(Z),14(Z)-trien-5-ynoic acid, Compound (D) when $R^{1'}$ is H. This reaction is effected through the di- Grignard derivative of 5-hexynoic acid. Thus, a solution of the acid in an anhydrous ethereal solvent, preferably tetrahydrofuran, is treated under an inert atmosphere with 2 molar equivalents of a Grignard reagent, such as a 3 to 4N solution of ethylmagnesium bromide, preferably at room temperature for about 1 hour. The solution is then heated by reflux temperature, and treated with stoichiometric amounts of a cuprous salt, particularly cuprous iodide, and hydroxylamine hydrochloride, in the presence of hexamethylphosphoramide. After a short refluxing period, of the order of 15 minutes to 1 hour, preferably for about 30 minutes, there is added a solution of Compound (XV) in an inert solvent, preferably the same ether solvent used for dissolving the acid reagent. The coupling reaction is also conducted at reflux temperature, for a period of time of between 8 to 16 hours, depending upon the starting iodo compound. The course of the reaction is followed by TLC analysis. Although the reaction consumes the reactants in molar basis, it is preferred to use a 5:1 molar ratio of 5-hexynoic acid: iodo compound.

Compound (D), is isolated from the reaction mixture by the methods known in the art. However, because the acid is unstable, it is preferred to purify compond (D) as the methyl ester. Thus, the crude acid is conventionally treated with ethereal diazomethane, and once the methyl ester has been obtained in pure form, the —$CH_3$ moiety is cleaved by alkaline treatment. In the preferred embodiments, this hydrolysis is effected with 3 molar equivalents of lithium hydroxide in aqueous dimethoxyethane solution, at room temperature for about 2 to 20 hours, depending upon the starting compound.

In an alternative method, as ester of 5-hexynoic acid, preferably the methyl ester is substituted for the free acid, and butyl lithium is used in place of the Grignard reagent. The reaction is also conducted under anhydrous conditions and under an inert atmosphere. Initially, a solution of the methyl ester of 5-hexynoic acid in an ethereal solvent, preferably tetrahydrofuran, is reacted with equimolar amounts of butyl lithium, at a temperature of about −70° C. for a period of time of between 30 minutes to 2 hours, preferably for about 45 minutes, followed by the addition of a cuprous salt, preferably cuprous iodide. After a few minutes, Compound (XV) is added, and the mixture is stirred at between −10 to 10° C., preferably at 0° C. for between 1 to 5 hours, preferably for about 3 hours. A molar ratio of 2 moles of compound (XIV): one mole of Compound (XV): and one mole of cuprous iodide is preferred.

The methyl ester thus obtained compound (D) when $R^{1'}$ is Me is hydrolyzed under alkaline conditions, preferably with lithium hydroxide in aqueous dimethoxyethane, as previously described.

The free acids of the present invention encompassed by formula (A) can be converted into esters other than those obtained as intermediates by the esterification methods known in the art, preferably by treatment with an excess of a diazoalkane such as diazomethane, diazoethane, diazopropane and the like in ether solution.

Alternatively, the esters can be prepared through the sodium salt, which is in turn reacted with an alkyl halide, preferably an alkyl bromide. The sodium salt is conveniently obtained by treatment of the free acid with between 1 and 1.1 molar equivalents of sodium methoxide in an inert organic solvent, preferably methanol, at room temperature. Thereafter the sodium salt is reacted with between 1 to 1.1 molar equivalents of the desired alkyl halide, for example, methyl bromide, isopropyl bromide, n-butyl bromide and the like in an inert organic solvent, preferably dimethyl sulfoxide, at a temperature of between 0° C. to 35° C., preferably room temperature, for between 2 to 6 hours.

The pharmaceutically acceptable salts of the free acids of the present invention of formula (A), when R is H, are prepared by treatment of the acid compound with at least one molar equivalent of an inorganic or an organic base. Typical bases used as reagents include sodium hydroxide, potassium hydroxide, ammonium hydroxide, calcium hydroxide, diethylamine, tromethamine, lysine, caffeine and the like. The reaction is conducted in water, alone or in combination with an inert, water-miscible organic solvent, at a temperature of from about 0° C., to about 50° C., preferably at room temperature. Typical inert, water miscible organic solvents include methanol, ethanol, isopropanol, butanol, acetone, dioxane or tetahydrofuran. The molar ratio of the free acid to base used are chosen to provide the ratio desired for any particular salt.

The majority of the compounds of the present invention are unstable and therefore it is convenient to store them at low temperature, preferably below −70° C.

In summary, the compounds of this invention can be made by reacting (III) with (IV), reacting (XV) with 5-hexynoic acid, deesterifying esters of formula (A), esterifying acids of formula (A), forming salts of formula (A) from acids of formula (A), and forming acids of formula (A) from salts of formula (A).

EXAMPLES

The following specific Preparations and Examples are given to enable the skilled artisan to more clearly understand and practice the present invention. The Examples and Preparations are not to be considered as limiting the scope of the claims, but are merely illustrative and representative thereof.

PREPARATION 1

Phenylpropargyl ethers

To a solution of 10.8 g (0.1 mol) of p-cresol in 70 ml of absolute ethanol, there were added 4 g of sodium hydroxide. The reaction mixture was refluxed until complete dissolution and then treated with 16.36 g (0.1 mol) of propargyl bromide (80% in toluene). Reflux was resumed for 14 additional hours. The reaction mixture was then cooled, poured into water and extracted with hexane (3×100 ml). The combined organic extracts were washed with 20% aqueous sodium hydroxide solution and water, dried over sodium sulfate and the solvent removed by evaporation. The residue was distilled at 102° C./15 mm to yield 3-(p-methylphenoxy)-1-propyne, identical to an authentic sample.

In a similar manner, substituting:
m-fluorophenol,
o-bromophenol,
m-bromophenol,
p-ethylphenol,
o-ethoxyphenol,
m-ethoxyphenol,
p-butylphenol,
m-trifluoromethylphenol,
p-trifluoromethylphenol,
o-cyanophenol and
p-cyanophenol for p-cresol there are respectively obtained:
3-(m-fluorophenoxy)-1-propyne;
3-(o-bromophenoxy)-1-propyne;
3-(m-bromophenoxy)-1-propyne;
3-(p-ethylphenoxy)-1-propyne;
3-(o-ethoxyphenoxy)-1-propyne;
3-(m-ethoxyphenoxy)-1-propyne;
3-(p-butylphenoxy)-1-propyne;
3-(m-trifluoromethylphenoxy)-1-propyne;
3-(p-trifluoromethylphenoxy)-1-propyne;
3-(o-cyanophenoxy)-1-propyne; and
3-(p-cyanophenoxy)-1-propyne.

PREPARATION 2

3-(p-methylthiophenoxy)-1-propyne

To a solution of 5.6 g of (p-methylthio)phenol in 32 ml of absolute ethanol, there were added 1.76 g of sodium hydroxide. The reaction mixture was refluxed until complete dissolution. Then 5.348 g of propargyl bromide (80% in toluene) was added. Reflux was resumed for 5 additional hours. Then the solution was cooled, poured into water and extracted with ether. The combined organic extracts were washed with 20% aqueous sodium hydroxide solution and water, dried over sodium sulfate and the solvent removed by evaporation. The residue was distilled at 152°-154° C./5 mm, to yield 3-(p-methylthiophenoxy)-1-propyne.

PREPARATION 3

Phenylpropargyl thioethers

A stirred solution of sodium ethoxide in ethanol, obtained from 6.89 g (0.3 m atoms) of sodium and 250 ml of absolute ethanol was treated by dropwise addition of 27.95 ml of thiophenol in 25 ml of absolute ethanol, while the temperature was maintained between 5°-10° C. The reaction mixture was stirred for 10 minutes, and cooled to 0° C. Then 36.46 ml (48.68 g, 0.40 mol) of propargyl bromide (80% in toluene) in 30 ml of absolute ethanol was added, to the reaction mixture, while the temperature was maintained at between 0°-10° C. After stirring for 30 additional minutes at 0°-10° C., the mixture was acidified with concentrated hydrochloric acid, poured into 300 ml of water, and extracted with hexane (2×500 ml). The organic extracts were washed with saturated sodium bicarbonate solution, dried and the solvent removed by evaporation. The residue was distilled at 52°/0.2 mm to yield of 3-phenylthio-1-propyne, identical to an authentic sample.

Likewise but using
o-thiocresol,
m-thiocresol,
p-thiocresol, and
4-mercaptoanisol
in place of thiophenol, there are prepared:
3-(0-methyl-thio-phenyl)-4-thio-phenyl;
3-(2-methyl-thio-phenyl)-1-propyne;
3-(2-methyl-thio-phenyl)-1-propyne;
3-(2-methyl-thio-phenyl)-1-propyne; and
3-(p-methoxy-thio-phenyl)-1-propyne, respectively.

PREPARATION 4

7-iodo-5-heptynoic acid ethyl ester

A. A mixture of 85 g of the tetrahydropyranyl ether of 7-hydroxy-5-heptynoic acid, (USP 3,801,623), 51 g of ethanol, 210 ml of benzene and 9 drops of concentrated sulfuric acid was refluxed for 3 hours under nitrogen atmosphere. The reaction mixture was cooled to room temperature and 85 ml of 12.5% aqueous sulfuric acid and 125 ml of ethanol were added thereto. The resulting mixture was stirred for 20 hours more at 20° C. The mixture was then neutralized by carefully adding saturated sodium carbonate solution and extracted with ether. The organic extract was washed with water, dried over sodium sulfate and the solvent removed by evaporation under reduced pressure. Column chromatography of the residue on 500 g of silica gel, using hexane:ethyl acetate (80:20) as eluant, yielded the ethyl ester of 7-hydroxy-5-heptynoic acid.

B. A solution of 7-hydroxy-5-heptynoic acid(0.18 mol) in 200 ml of anhydrous methylene chloride was cooled to 0° C., 40.7 ml (0.29 mol) of triethylamine was added to the cold solution, then 21 ml (0.27 mol) of mesyl chloride, in a dropwise fashion, while maintaining the temperature at 0° C. The resulting mixture was stirred at 0° C. for 30 minutes and then diluted with methylene chloride. The methylene chloride solution was washed with saturated sodium bicarbonate solution, dried over sodium sulfate and the methylene chloride evaporated under reduced pressure.

The crude mesylate obtained was dissolved in 107 ml of dimethylsulfoxide and treated with 81.47 g (0.54 mol) of sodium iodide in 150 ml of water and 30 ml of dimethyl sulfoxide. The resulting mixture was stirred at room temperature for 1 hour, then poured into water and extracted 4 times with ethyl acetate. The combined organic extracts were washed with water, dried over sodium sulfate and the solvent evaporated in vacuo. Purification of the residue by column chromatography on 300 g of silica gel, using hexane:ethyl acetate (90:10) as eluant, afforded 7-iodo-5-heptynoic acid ethyl ester, as an oil.

When methanol was substituted for ethanol in part A of this preparation there was obtained 7-iodo-5-heptynoic acid methyl ester as final product.

EXAMPLE 1

16-(p-methylphenoxy)hexadeca-5,8,11,14-tetraynoic acid

A. To a cold (0°–5° C.) solution of 16.73 g (0.11 mol) of 3-(p-methylphenoxy)-1-propyne (C.A., 82, 155636 d) in 120 ml of anhydrous tetrahydrofuran 32.28 ml (16.05 g, 0.12 mol) of a 3.73N solution of ethylmagnesium bromide in ether was added dropwise under argon, at such a rate to maintain the temperature at 0° C. Thereafter, the reaction mixture was stirred for 1 hour further at 0°–5° C. Then, 564 mg of cuprous cyanide were added. After stirring 20 minutes more, a solution of 9 g (0.057 mol) of 1-bromo-2,5-hexadiyne [R.I. Fryer, et al., *J. Org. Chem.*, 40, 348 (1975)], in 25 ml of anhydrous tetrahydrofuran was added dropwise, and the temperature maintained at between 0°–5° C. The reaction mixture was stirred at room temperature for 3 additional hours, and then poured into 200 ml of 1N sulfuric acid and ice. After extraction with ether (3×250 ml) the combined organic extracts were concentrated in vacuo to a small volume, and washed several times with aqueous EDTA to remove the copper salts, and then with water. The organic extracts were then dried over sodium sulfate and the organic solvent removed by evaporation.

The crude material was purified by column chromatography on 500 g of silica gel, using hexane:ethyl acetate (98:2) as eluant, and the product crystallized from methylene chloride-hexane, to yield 9-(p-methylphenoxy)-1,4,7-nonatriyne, M.P. 34.5°–35.5° C. The product was stored in dry ice.

B. 9.57 ml (4.75 g, 35.67 mmol) of 3.73N ethylmagnesium bromide in ether was added, dropwise, under argon to a solution of 7.92 g (35.67 mmol) of 9-(p-methylphenoxy)-1,4,7-nonatriyne in 80 ml of anhydrous tetrahydrofuran. The temperature was maintained at 0° C. The reaction mixture was stirred for 1 hour further at 0° C. and then allowed to warm to room temperature. Then 270 mg of cuprous cyanide was added to the warmed mixture. The mixture was stirred for 20 minutes, heated to 40° C. and treated with 7.3 g (27.44 mmol) of 7-iodo-5-heptynoic acid methyl ester. The resulting mixture stirred for 4 hours while the temperature was maintained at 40° C. The reaction mixture was then poured into 300 ml of 1N sulfuric acid and ice and extracted with ether (3×250 ml). The combined organic extract was concentrated to about 1/5 its original volume and washed several times with EDTA and water, dried over sodium sulfate and the solvent removed by evaporation in vacuo. The crude material was purified by column chromatography on 400 g of silica gel, using hexane:ethyl acetate (98:2) as eluant, yielding a 3:1 mixture of the methyl and ethyl esters of 16-(p-methylphenoxy)hexadeca-5,8,11,14-tetraynoic acid, as an oil. The mixture was stored in dry ice.

This mixture can be separated into the individual esters by thin layer chromatography. The ethyl ester has the following constants:

| | MeOH | |
|---|---|---|
| U.V. | λmax 228, 280 nm (ε 5495, 1778) | |
| I.R. | (CHCl₃) | 1000, 1310 1610, 1740, 2920 cm⁻¹ |
| N.M.R. | (CdCl₃) | 1.26 (t, 3H) |
| | | 1.83 (m, 2H) |
| | | 2.16 (t, 2H) |
| | | 2.3 (s, 3H) |
| | | 2.4 (t, 2H) |
| | | 3.15 (s, 6H) |
| | | 4.11 (m, 2H) |
| | | 4.63 (s, 2H) |
| | | 6.73–7.33 (m, 4H) |
| M.S. | | 374 (M⁺). |

C. 770 mg of the foregoing mixture of 16-(p-methylphenoxy)hexadeca-5,8,11,14-tetraynoic acid esters were treated with 168 ml of a pH 6.7 buffer solution prepared by mixing 100 ml of 0.1M disodium hydrogen phosphate and 100 ml of 0.1M potassium dihydrogen phosphate. The mixture was vigorously stirred and 15.96 g of Sigma Lipase, Type VII, from Candida cylindracea was added, stirring was continued for 18 hours at room temperature. The reaction mixture was then transferred to a separatory funnel, and 200 ml of ethyl acetate was added. The solution was then acidified with a saturated solution of oxalic acid. The organic layer was separated, dried over sodium sulfate and the solvent removed under vacuo. The residue was purified in the Chromatotron using hexane:ethyl acetate:acetic acid (60:40:1) as gradient. The crude product was crystallized from benzene-hexane, to yield 16-(p-methylphenoxy)hexadeca-5,8,11,14-tetraynoic acid. M.P. 70°–71° C. (dec) (Recrystallized from benzene-hexane), which was stored in dry ice.

EXAMPLE 2

16-(p-methylphenoxy)hexadeca-5(Z),8(Z),11(Z),14(Z)-tetraenoic acid

A. A solution of 423.6 mg (1.13 mmol) of 16-(p-methylphenoxy)hexadeca-5,8,11,14-tetraynoic acid ethyl ester in 15 ml of a (1:1) mixture of methanol:ethyl acetate was hydrogenated at room temperature and atmospheric pressure (585 mm) in the presence of 84 mg of prereduced Lindlar's catalyst and 0.05 ml of quinoline, until the calculated amount of hydrogen was consumed (146 ml). The catalyst was separated by filtration through Celite and the filtrate evaporated in vacuo. The residue was purified by thin layer chromatography, using hexane:ethyl methyl ketone (98:2) as gradient, to yield 16-(p-methylphenoxy)hexadeca-5(Z),8(Z),11(Z),14(Z)-tetraenoic acid ethyl ester, as an oil.

| | MeOH | |
|---|---|---|
| U.V. | λmax 230, 281 nm (ε 6918, 1445) | |
| I.R. | (CHCl₃) | 1000, 1230, 1510, 1600, 1730, 2930 cm⁻¹ |
| N.M.R. | (CdCl₃) | 1.23 (t, 3H) |
| | | 1.7 (m, 2H) |
| | | 2.03 (t, 2H) |
| | | 2.31 (t, 5H) |
| | | 2.81 (t, 6H) |

-continued

| | |
|---|---|
| | 4.08 (m, 2H) |
| | 4.53 (d, 2H) |
| | 5.2–5.86 (m, 8H) |
| | 7.66–7.33 (m, 4H) |
| M.S. | 383 (M+). |

This product was stored in dry ice.

B. A solution of 79.5 mg of 16-(p-methylphenoxy)-hexadeca-5(Z),8(Z),11(Z),14(Z)-tetraenoic acid ethyl ester in 10 ml of 90% aqueous methanol was treated with 1.66 ml of a 0.5N sodium hydroxide solution. The reaction mixture was stirred at room temperature for 48 hours. The solvent was then evaporated in vacuo and the residue diluted with 10 ml of water, acidified with saturated solution of oxalic acid and extracted with ethyl acetate (3×30 ml). The combined organic extracts were dried over sodium sulfate and the solvent evaporated in vacuo. The residue was purified by column chromatography on 10 g of silica gel, using methylene chloride-methanol (95:5) as eluant, to yield 16-(p-methylphenoxy)hexadeca-5(Z),8(Z),11(Z),14(Z)-tetranoic acid, as an oil.

| | MeOH | |
|---|---|---|
| U.V. | λmax 228, 280 nm | |
| | (ε 8128, 1514) | |
| I.R. | (CHCl$_3$) | 1230, 1510, 1615, 1720, 2800–3300 cm$^{-1}$ |
| N.M.R. | (CdCl$_3$) | 1.73 (m, 2H) |
| | | 2.06 (t, 2H) |
| | | 2.35 (t, 5H) |
| | | 2.83 (m, 6H) |
| | | 4.55 (d, 2H) |
| | | 5.2–5.76 (m, 8H) |
| | | 6.66–8.33 (m, 5H) |
| M.S. | | 354 (M+). |

EXAMPLE 3

16-(m-methylophenoxy)hexadeca-5,8,11,14-tetraynoic acid

A. 14.55 ml (6.79 g, 50.9 mmol) of a 3.5N solution of ethylmagnesium bromide in ether was added dropwise, under argon to a cold (0°–5° C.) solution of 7.82 g (53 mmol) of 3-(methylphenoxy)-1-propyne (C.A. 82, 155636 d) in 150 ml of anhydrous tetrahydrofuran at such a rate to maintain the temperature at 0° C. Thereafter, the reaction mixture was stirred for 1 hour further at 0°–5° C. Then, 246 mg of cuprous cyanide was added. After stirring 20 minutes more, a solution of 4 g (25.4 mmol) of 1-bromo-2,5-hexadiyne in 25 ml of anhydrous tetrahydrofuran was added dropwise, maintaining the temperature between 0°–5° C. The mixture was stirred at room temperature for 3 additional hours, and poured into 200 ml of 1N sulfuric acid and ice. After extraction with ether (3×100 ml) the combined organic extracts were concentrated in vacuo to a small volume, and washed several times with EDTA, to remove the copper salts, and then with water, dried over sodium sulfate and evaporated. The crude material was purified by column chromatography on 250 g of silica gel, using hexane as eluant, to yield 9-(m-methylphenoxy)-1,4,7-nonatriyne, as an oil. The product was stored in dry ice.

B. 1.61 ml (751 mg, 5.6 mmol) of 3.6N ethylmagnesium bromide in ether was added dropwise, under argon to a solution of 1.34 g (6 mmol) of 9-(m-methylphenoxy)-1,4,7-nonatriyne in 20 ml of anhydrous tetrahydrofuran. The temperature was maintained at 0° C. The reaction mixture was stirred for one hour further at 0° C., then allowed to warm to room temperature, and then 50 mg of cuprous cyanide was added. The mixture was stirred for 20 minutes, heated to 40° C. and then 1 g (3.75 mmol) of 7-iodo-5-heptynoic acid methyl ester was added. The resulting mixture was stirred during 4 hours at 40° C. The reaction mixture was then poured into 60 ml of 1N sulfuric acid and ice and the product extracted with ether (3×100 ml). The combined organic extract was concentrated to about 1/5 its original volume and washed several times with EDTA and water, dried over sodium sulfate and evaporated in vacuo. The crude material was purified by column chromatography on 75 g of silica gel, using hexane:ethyl acetate (85:15) as eluant, to obtain 16-(m-methylphenoxy)hexadeca-5,8,11,14-tetraynoic acid methyl ester, as an oil. The product was stored in dry ice.

| | MeOH | |
|---|---|---|
| U.V. | λmax 224, 273 279 nm | |
| | (ε 7413, 2089, 1950) | |
| I.R. | (CHCl$_3$) | 2195, 1735, 1615 cm$^{-1}$ |
| N.M.R. | (CdCl$_3$) | 1.86 (m, 2H) |
| | | 2.13–2.6 (m, 7H) |
| | | 3.16 (s, 6H) |
| | | 3.7 (s, 3H) |
| | | 4.66 (s, 2H) |
| | | 6.66–7.33 (m, 4H) |
| M.S. | | 360 (M+). |

C. 185 mg of 16-(m-methylphenoxy)hexadeca-5,8,11,14-tetraynoic acid methyl ester was treated with 21 ml of a pH 6.7 buffer solution (prepared as described in Example 1) and 1.98 g of Sigma Lipase, Type VII, from Candida cylindracea and sonicated for 30 minutes at room temperature. The reaction mixture was then transferred to a separatory funnel with ethyl acetate (200 ml) and acidified to pH ~3 with a saturated solution of oxalic acid. The organic layer was separated, dried over sodium sulfate and the solvent removed in vacuo. The residue was purified by thin layer chromatography in silica gel with a Chromatatron (model 7924, Harrison Research, Palo Alto, CA) using hexane:ethyl acetate:acetic acid (70:30:1) as the eluant, yielding 16-(m-methylphenoxy)-hexadeca-5,8,11,14-tetraynoic acid, as an oil. The product was stored in dry ice.

| | MeOH | |
|---|---|---|
| U.V. | λmax 228, 272 279 nm | |
| | (ε 4363, 2344, 2239) | |
| I.R. | (CHCl$_3$) | 3060, 2180, 1720 1615 cm$^{-1}$ |
| N.M.R. | (CdCl$_3$) | 1.783 (m, 2H) |
| | | 2.13–2.6 (m, 7H) |
| | | 3.13 (s, 6H) |
| | | 4.63 (s, 2H) |
| | | 6.63–7.33 (m, 4H) |
| | | 9.63 (s, broad 1H) |
| M.S. | | 346 (M+). |

EXAMPLE 4

16-(m-methylphenoxy)hexadeca-5(Z),8(Z),11(Z),14(Z)-tetraynoic acid

A. A solution of 79 mg (0.219 mmol) of 16-(m-methylphenoxy)hexadeca-5,8,11,14-tetraynoic acid methyl ester in 10 ml of a (1:1) mixture of methanol-ethyl acetate was hydrogenated at room temperature in the presence of 8 mg of prereduced Lindlar's catalyst and 0.022 ml (0.188 mmol) of quinoline, until the calculated amount of hydrogen was consumed (27.6 ml) (at 585 mm). The catalyst was separated by filtration through Celite and the filtrate evaporated in vacuo. The residue was purified by thin layer chromatography on silica gel with a Chromatotron, using hexane-ethyl acetate (90:10) as the eluant, to yield 16-(m-methylphenoxy)hexadeca-5(Z),8(Z),11(Z),14(Z)-tetraenoic acid methyl ester, as an oil.

| | MeOH | |
|---|---|---|
| U.V. | λmax 230, 274.5, 280.5 nm | |
| | (ε 4677, 1202, 1202) | |
| I.R. | (CHCl$_3$) | 2910, 1735, 1615 cm$^{-1}$ |
| N.M.R. | (CdCl$_3$) | 1.7 (m, 2H) |
| | | 1.96–2.15 (m, 7H) |
| | | 2.86 (t, 6H) |
| | | 3.66 (s,3H CO$_2$CH$_3$) |
| | | 4.63 (d, 2H) |
| | | 5.15–5.93 (m, 8H) |
| | | 6.63–7.33 (m, 4H) |
| M.S. | | 386 (M + NH$_4$)$^+$. |

This product was stored in dry ice.

B. A solution of 183 mg of 16-(m-methylphenoxy)-hexadeca-5(Z),8(Z),11(Z),14(Z)-tetraenoic acid methyl ester in 15 ml of methanol was treated with 2.5 ml of 0.5N sodium hydroxide solution, the reaction mixture was stirred at room temperature during 36 hours. The solvent was then evaporated in vacuo and the residue diluted with 10 ml of water, acidified to pH 3 with saturated solution of oxalic acid and extracted with ethyl acetate (3×50 ml). The combined organic extracts were dried over sodium sulfate and the solvent removed by evaporation in vacuo.

Purification of the residue by thin layer chromatography (TLC) on silica gel with a Chromatotron using hexane:ethyl acetate:acetic acid (90:10:1) as eluant afforded 16-m-methylphenoxy)-hexadeca-5(Z),8(Z),11(Z),14(Z)-tetraenoic acid, as an oil.

| | MeOH | |
|---|---|---|
| U.V. | λmax 221, 273.5, 280 nm | |
| | (ε 7244, 1820, 1660) | |
| I.R. | (CHCl$_3$) | 3070, 2910, 1715, 1615 cm$^{-1}$ |
| N.M.R. | (CdCl$_3$) | 1.7 (m, 2H) |
| | | 1.93–2.53 (m, 7H) |
| | | 2.83 (t, 6H) |
| | | 4.6 (d, 2H) |
| | | 5.16–5.9 (m, 8H) |
| | | 6.6–7.33 (m, 4H) |
| | | 7.83 (s, broad 1H, CO$_2$H) |
| M.S. | | 355 (M$^+$). |

EXAMPLE 5

16-phenoxyhexadeca-5,8,11,14-tetraynoic acid

A. 4.81 ml (1.92 g, 14.4 mmol) of a 3N solution of ethylmagnesium bromide in ether was added dropwise under argon to a solution of 2 g (15.15 mmol) of 3-phenoxy-1-propyne (G. Pourcelot, et al., Bull. Soc. Chim., France, (1966), pp 3016–24, in 15 ml of anhydrous tetrahydrofuran. The rate of addition was adjusted to maintain the temperature at 0° C. Thereafter, the reaction mixture was stirred for 1 hour further at 0°–5° C. Then, 77 mg of cuprous cyanide was added. After stirring 20 minutes more, a solution of 1.13 g (7.22 mmol) of 1-bromo-2,5-hexadiyne in 10 ml of anhydrous tetrahydrofuran was added dropwise. The temperature was maintained at between 0°–5° C. The resulting mixture was stirred at room temperature for 3 additional hours, then poured into 60 ml of 1N sulfuric acid and ice, and the resulting solution extracted with ether (3×100 ml). The combined organic extracts were concentrated in vacuo to a small volume, and washed several times with EDTA and water, dried over sodium sulfate and evaporated. The crude material was purified by TLC using hexane:methylene chloride (80:20) as the eluant, and the product crystallized from methylene chloride-hexane, to yield 9-phenoxy-1,4,7-nonatriyne, as an oil. The product was stored in dry ice.

B. 3 ml (1.2 g, 9 mmol) of 3N ethylmagnesium bromide in ether was added dropwise, under argon to a solution of 2 g (9.6 mmol) of 9-phenoxy-1,4,7-nonatriyne in 20 ml of anhydrous tetrahydrofuran. The temperature was maintained at 0° C. After addition the reaction mixture was stirred for 1 hour further at 0° C., then allowed to warm to room temperature. Then 59 mg of cuprous cyanide was added, and the mixture stirred for 20 minutes, heated to 40° C. and then treated with 1.59 g (6 mmol) of 7-iodo-5-heptynoic acid methyl ester. The resulting mixture was stirred an additional 4 hours at 40° C.

The reaction mixture was then poured into 120 ml of 1N sulfuric acid and ice and the product extracted with ether (3×100 ml). The combined organic extract was concentrated to about 1/5 its original volume and washed several times with EDTA and water, dried over sodium sulfate and evaporated in vacuo. The crude material was purified by column chromatography on 100 g of silica gel, using hexane:ether (80:20) as eluant, to obtain 16-phenoxyhexadeca-5,8,11,14-tetraynoic acid methyl ester, as an oil. The product was stored in dry ice.

| | MeOH | |
|---|---|---|
| U.V. | λmax 225, 271.5, 278 nm | |
| | (ε 5248, 2188, 1195) | |
| I.R. | (CHCl$_3$) | 1000, 1255, 1600, 1740, 2870 cm$^{-1}$ |
| N.M.R. | (CdCl$_3$) | 1.83 (m, 2H) |
| | | 2.23 (t, 2H) |
| | | 2.43 (t, 2H) |
| | | 3.16 (s, 6H) |
| | | 3.66 (s, 3H) |
| | | 4.66 (s, 2H) |
| | | 6.83–7.46 (m, 5H) |
| M.S. | | 364 (M + NH$_4$). |

C. 540 mg of 16-phenoxyhexadeca-5,8,11,14-tetraynoic acid methyl ester were treated with 64 ml of a pH 6.7 buffer solution (disodium hydrogen phosphate-potassium dihydrogen phosphate) obtained as described in Example 1. The emulsion was vigorously stirred and 6.17 g of Sigma Lipase, Type VII, from Candida cylindracea was added, stirring for 8 hours at room temperature. The reaction mixture was then transferred to a separatory funnel with ethyl acetate (100 ml), and then acidified with saturated solution of oxalic acid. The organic phase was separated, dried over sodium sulfate and the solvent removed under vacuo. The residue was purified by TLC on silica gel with a Chromatotron using hexane:ethyl acetate:acetic acid (60:40:1) as the eluant. The crude product was crystallized from benzene-hexane, to yield 16-phenoxyhexadeca-5,8,11,14-tetraynoic acid. M.P. 74°–76° C. (dec.). The product was stored in dry ice.

EXAMPLE 6

16-phenoxyhexadeca-5(Z),8(Z),11(Z),14(Z)-tetraenoic acid

A. A solution of 100 mg (0.289 mmol) of 16-phenoxyhexadeca-5,8,11,14-tetraynoic acid methyl ester in 10 ml of a (1:1) mixture of methanol-ethyl acetate was hydrogenated at room temperature in the presence of 10 mg of prereduced Lindlar's catalyst and 0.028 ml of quinoline, until the calculated amount of hydrogen was consumed (36 ml) (585 mm). The catalyst was separated by filtration through Celite and the filtrate evaporated in vacuo. The residue was purified by thin layer chromatography, using hexane:acetone (99:1) as gradient, to yield 16-phenoxyhexadeca-5(Z),8(Z),11(Z), 14(Z)-tetraenoic acid methyl ester, as an oil.

| | MeOH | |
|---|---|---|
| U.V. | λmax 226, 273, 280 nm | |
| | (ε 6166, 1445, 1259 | |
| I.R. | (CHCl$_3$) | 1210, 1490, 1600, 1690, 2940 cm$^{-1}$ |
| N.M.R. | (CdCl$_3$) | 1.66 (m, 2H) |
| | | 2.05 (t, 2H) |
| | | 2.3 (t, 2H) |
| | | 2.83 (t, 6H) |
| | | 3.63 (s, 3H) |
| | | 4.6 (d, 2H) |
| | | 5.23–5.9 (m, 8H) |
| | | 6.8–7.46 (m, 5H) |
| M.S. | | 355 (MH$^+$). |

The product was stored in dry ice.

B. A solution of 23 mg of 16-phenoxyhexadeca-5(Z),8(Z),11(Z),14(Z)-tetraenoic acid methyl ester in 5 ml of 90% aqueous methanol was treated with 0.29 ml of 0.5N sodium hydroxide solution. The reaction mixture was stirred at room temperature for 48 hours. The solvent was then evaporated in vacuo and the residue diluted with 10 ml of water, acidified with saturated solution of oxalic acid and extracted with ethyl acetate (2×30 ml). The combined organic extract were dried over sodium sulfate and evaporated in vacuo. The residue was purified by TLC on silica gel with a Chromatotron, using hexane:ethyl acetate-acetic acid (90:10:1) as the eluant, to yield 16-phenoxyhexadeca-5(Z),8(Z),11(Z),14(Z)-tetraenoic acid, as an oil.

| | MeOH | |
|---|---|---|
| U.V. | λmax 226.5, 273, 279 nm | |
| | (ε 7244, 1622, 1380) | |
| I.R. | (CHCl$_3$) | 1220, 1490, 1600, 1715, 2500, 3600 cm$^{-1}$ |
| N.M.R. | (CdCl$_3$) | 1.73 (m, 2H) |
| | | 2.08 (t, 2H) |
| | | 2.33 (t, 2H) |
| | | 2.83 (t, 6H) |
| | | 4.58 (d, 2H) |
| | | 5.26–5.96 (m, 8H) |
| | | 6.73–7.5 (m, 5H) |
| | | 8.2 (s, 1H) |
| M.S. | | 341 (MH$^+$). |

EXAMPLE 7

16-(m-chlorophenoxy)hexadeca-5,8,11,14-tetraynoic acid

A. 21.76 ml (9.8 g, 0.735 mmol) of a 3.38N solution of ethylmagnesium bromide in ether was added dropwise, under argon to a cold (0°–5° C.) solution of 11.66 g (0.7 mol) of 3-(m-chlorophenoxy)-1-propyne [I. Iway, et al., Chem. Pharm. Bull., 11, 1042 (1963)] in 80 ml of anhydrous tetrahydrofuran. The rate was monitored to maintain a temperature of 0° C. Thereafter, the reaction mixture was stirred for 1 hour further at 0°–5° C. Then, 31.35 mg of cuprous cyanide were added and the mixtured stirred 20 minutes more. Then a solution of 5.5 g (0.035 mol) of 1-bromo-2,5-hexadiyne in 20 ml of anhydrous tetrahydrofuran was added dropwise to the mixture as the temperature was maintained at between 0°–5° C. Then the reaction was stirred at room temperature for 3 additional hours and quenched with 200 ml of 1N sulfuric acid and ice. After extraction with ether (3×200 ml), the combined organic extracts were concentrated in vacuo to a small volume, and washed several times with EDTA and water, dried over sodium sulfate and evaporated in vacuo. The residue was purified by column chromatography on 350 g of silica gel, using hexane as eluant, and the product crystallized from methylene chloride-hexane, to yield 9-(m-chlorophenoxy)-1,4,7-nonatriyne, as an oil. The product was stored in dry ice.

B. 3.38N ethylmagnesium bromide in ether was added dropwise, under argon to a solution of 300 mg (1.237 mmol) of 9-(m-chlorophenoxy)-1,4,7-nonatriyne in 10 ml of anhydrous tetrahydrofuran. The temperature was maintained at 0° C. Then the reaction mixture was stirred for 1 hour further at 0° C., then allowed to warm to room temperature. Then 12.1 mg of cuprous cyanide were added and this mixture stirred for 20 minutes, then heated to 40° C. and treated with 493 mg (1.85 mmol) of 7-iodo-5-heptynoic acid methyl ester. This mixture was then stirred for 3.5 hours at 40° C.

The reaction mixture was then poured into 25 ml of 1N sulfuric acid and ice and the product extracted with ether (3×50 ml). The combined organic extract was concentrated to a small volume and washed several times with EDTA and water, dried over sodium sulfate and evaporated in vacuo. The crude material was purified by column chromatography on 15 g of silica gel, using hexane as eluant, to obtain a mixture of the methyl and ethyl esters of 16-(m-chlorophenoxy)hexadeca-5,8,11,14-tetraynoic acid, as an oil. These compounds were separated by thin layer chromatography, using hexane:ethyl acetate (90:10) the eluant (3 developments), to yield the two esters, both oily products.

| Methyl ester: | | |
|---|---|---|
| | MeOH | |
| U.V. | λmax 229, 274 nm | |
| | (ε 4467, 2630) | |
| I.R. | (CHCl$_3$) | 1000, 1330, 1470, 1600, 1730, 2940 cm$^{-1}$ |
| N.M.R. | (CdCl$_3$) | 1.83 (m, 2H) |
| | | 2.23 (t, 2H) |
| | | 2.43 (t, 2H) |
| | | 3.16 (t, 6H) |
| | | 3.66 (s, 3H) |
| | | 4.66 (t, 2H) |
| | | 6.75–7.36 (m, 4H) |
| Ethyl ester: | | |
| | MeOH | |
| U.V. | λmax 230, 274 nm | |
| | (ε 7243, 5563) | |
| I.R. | (CHCl$_3$) | 990, 1310, 1590, 1730, 2940 cm$^{-1}$ |
| N.M.R. | (CdCl$_3$) | 1.26 (t, 3H) |
| | | 1.83 (m, 2H) |
| | | 2.2 (d, 2H) |
| | | 2.4 (t, 2H) |
| | | 3.16 (d, 6H) |
| | | 4.13 (m, 2H) |
| | | 4.66 (s, 2H) |

|       |                    |
|-------|--------------------|
|       | 6.73–7.36 (m, 4H)  |
| M.S.  | 412 (M—NH₄)⁺.     |

C. To 935 mg of the mixture of esters there were added 96.75 ml of a pH-6.7 buffer solution of disodium hydrogen phosphate and potassium dihydrogen phosphate, prepared as described in Example 1 and 9.19 g Sigma Lipase, type VII from Candida cylindracea. The reaction mixture was stirred for 2 hours at room temperature and then 4.5 g more of the enzyme and 45 ml of buffer solution were added. Stirring was continued for 10 hours. The reaction mixture was then transferred to a separatory funnel with ethyl acetate (200 ml) and acidified with saturated oxalic acid solution. The organic layer was separated, dried over sodium sulfate and the solvent removed under reduced pressure. The residue was purified by TLC on silica gel with a Chromatotron using hexane-ethyl acetate-acetic acid (60:40:1) as the eluant. The product was crystallized from benzene-hexane to yield 43.2 mg (5%) of 16-(m-chlorophenoxy)hexadeca-5,8,11,14-tetraynoic acid. M.P. 32° C. (dec). The product was stored in dry ice.

EXAMPLE 8

16-(m-chlorophenoxy)hexadeca-5(Z),8(Z),11(Z),14(Z)-tetraenoic acid

A solution of 337.8 mg (0.85 mmol) of 16-(m-chlorophenoxy)hexadeca-5,8,11,14-tetraynoic acid ethyl ester in 30 ml of a (1:1) mixture of methanol-ethyl acetate was hydrogenated at room temperature in the presence of 60 mg of pre-reduced Lindlar's catalyst and 0.04 ml of quinoline, until the calculated amount of hydrogen was consumed (110 ml) (585 mm). The catalyst was separated by filtration through Celite and the filtrate evaporated in vacuo. The residue was purified by thin layer chromatography, using hexane-acetone (99:1) as gradient, to yield 16-(m-chlorophenoxy)-hexadeca-5(Z),8(Z),11(Z),14(Z)-tetraenoic acid ethyl ester, as an oil.

|        | MeOH                                          |
|--------|-----------------------------------------------|
| U.V.   | λmax 214, 275.5 nm                            |
|        | (ε 10, 720, 1820)                             |
| I.R.   | (CHCl₃)  1000, 1220, 1600, 1730, 2930, cm⁻¹   |
| N.M.R. | (CdCl₃)  1.23 (t, 3H)                         |
|        | 1.73 (m, 2H)                                  |
|        | 2.06 (t, 2H)                                  |
|        | 2.3 (t, 2H)                                   |
|        | 2.83 (t, 6H)                                  |
|        | 4.13 (m, 2H)                                  |
|        | 4.56 (d, 2H)                                  |
|        | 5.1–5.86 (m, 8H)                              |
|        | 6.66–7.14 (m, 4H)                             |
| M.S.   | 420 (M—NH₄)⁺.                                 |

This product was stored in dry ice.

Upon hydrolysis of 16-(m-chlorophenoxy)-hexadeca-5(Z), 8(Z),11(Z),14(Z)-tetraenoic acid ethyl ester with sodium hydroxide in aqueous methanol, in accordance with the method of Example 2, Part B, 16-(m-chlorophenoxy)-hexadeca-5(Z),8(Z),11(Z),14(Z)-tetraenoic acid, as an oil was obtained.

|        | MeOH                                    |
|--------|-----------------------------------------|
| U.V.   | λmax 220, 277 nm                        |
|        | (ε 8511, 1380)                          |
| I.R.   | (CHCl₃)  1000, 1480, 1600, 1720, 2800,  |
|        | 3300 cm⁻¹                               |
| N.M.R. | (CdCl₃)  1.73 (m, 2H)                   |
|        | 2.06 (t, 2H)                            |
|        | 2.35 (t, 2H)                            |
|        | 2.83 (t, 6H)                            |
|        | 4.56 (d, 2H)                            |
|        | 5.13–5.86 (m, 8H)                       |
|        | 6.66–7.33 (m, 4H)                       |
|        | 9.1 (s broad, 1H COOH)                  |
| M.S.   | 392 (M—NH₄)⁺.                           |

EXAMPLE 9

16-phenylthiohexadeca-5,8,11,14-tetraynoic acid

A. 24.64 ml (12.48 g, 0.0936 mol) of a 3.8N solution of ethylmagnesium bromide in ether was added dropwise, under argon to a cold solution of 13.2 g (0.089 mol) of 3-phenylthio-1-propyne (G. Pourcelot et al, vide supra) in 70 ml of anhydrous tetrahydrofuran. The temperature was maintained at 0°–5° C. Thereafter, the reaction mixture was stirred for 1 hour further at room temperature. Then, 440 mg of cuprous cyanide were added and the solution stirred for 20 minutes more. Then a solution of 7 g (0.0445 mol) of 1-bromo-2,5-hexadiyne in 20 ml of anhydrous tetrahydrofuran was added dropwise, maintaining the temperature between 0°–5° C. After the addition, the reaction mixture was stirred at room temperature for 3 additional hours, and then quenched with 150 ml of 1N sulfuric acid and ice. After extraction with ether (3×150 ml) the combined organic extracts were concentrated in vacuo to a small volume, and washed several times with EDTA and then with water, dried over sodium sulfate and evaporated. The crude material was purified by column chromatography on 150 g of silica gel, using hexane as eluant, to produce 9-phenylthio-1,4,7-nonatriyne, as an oil. The product was stored in dry ice.

B. 8.4 ml (4.254 g, 31 mmol) of 3.79N ethereal ethylmagnesium bromide was added dropwise, under argon to a solution of 6.5 g (29 mmol) of 9-phenylthio-1,4,7-nonatriyne in 20 ml of anhydrous tetrahydrofuran. The temperature was maintained at −25° C. After the addition, the reaction mixture was stirred for 1 hour further at the same temperature and then 285 mg of cuprous cyanide were added. After the addition, the mixture was stirred for 20 minutes more at 0° C. and then treated with 12.2 g (44 mmol) of 7-iodo-5-heptynoic acid ethyl ester in 15 ml of anhydrous tetrahydrofuran. After the addition, the solution was stirred for an additional 3 hours at room temperature. The reaction mixture was then poured into 150 ml of 1N sulfuric acid and ice and the product extracted with ether (3×150 ml). The combined organic extract was concentrated to about ⅓ its original volume and washed 3 times with EDTA and water, dried over sodium sulfate and evaporated in vacuo. The crude material was purified by column chromatography on 100 g of silica gel, using hexane-ethyl acetate (95:5) as eluant, to obtain 16-phenylthiohexadeca-5,8,11,14-tetraynoic acid ethyl ester, as an oil. The product was stored in dry ice.

|        | MeOH                                          |
|--------|-----------------------------------------------|
| U.V.   | λmax 252 nm                                   |
|        | (ε 5370)                                      |
| I.R.   | (CHCl₃)  1030, 1160, 1320, 1420, 1590, 1730,  |
|        | 2000 cm⁻¹                                     |
| N.M.R. | (CdCl₃)  1.23 (t, 3H COOCH₂CH₃)               |

| | | |
|---|---|---|
| | | 1.8 (m, 2H) |
| | | 2.2 (t, 2H) |
| | | 2.41 (t, 2H) |
| | | 3.16 (s, 6H) |
| | | 3.6 (s, 2H) |
| | | 4.13 (m, 2H COOCH$_2$CH$_3$) |
| | | 7.1–7.6 (m, 5H) |
| M.S. | | 377 MH$^+$. |

C. A mixture of 1.7 g of 16-phenylthiohexadeca-5,8,11,14-tetraynoic acid ethyl ester, 184 ml of the pH 6.7 buffer solution of disodium hydrogen phosphate/potassium dihydrogen phosphate, prepared as in Example 1 and 17.5 g of Sigma Lipase, Type VII, from Candida cylindracea was sonicated for 5 hours at room temperature. The reaction mixture was then transferred to a separatory funnel with ethyl acetate (200 ml) and acidified with saturated solution of oxalic acid. The organic phase was separated and combined with ethyl acetate extracts of the aqueous phase. The ethyl acetate was dried over sodium sulfate and removed under vacuo. The residue was purified by TLC on silica gel using a Chromatotron using hexane:ethyl acetate:acetic acid (60:40:1) as the eluant. The crude product was crystallized from methylene chloride-hexane, to yield 16-phenylthiohexadeca-5,8,11,14-tetraynoic acid. M.P. 69°–71° C. (dec), which was stored in dry ice.

EXAMPLE 10

16-phenylthiohexadeca-5(Z),8(Z),11(Z),14(Z)-tetraenoic acid

A. A solution of 1 g of 16-phenylthiohexadeca-5,8,11,14-tetraynoic acid ethyl ester in 50 ml of a 1:1 mixture of methanol:ethyl acetate was hydrogenated at room temperature in the presence of 200 mg of pre-reduced Lindlar's catalyst and 0.125 ml of quinoline. When the calculated amount of hydrogen was consumed (338 ml) (585 mm), the catalyst was separated by filtration through Celite and the filtrate evaporated in vacuo. The residue was purified by column chromatography on 50 g of silica gel, using hexane-ethyl acetate (98:2) as the eluting solvent, to yield 634.5 mg (62%) of 16-phenylthiohexadeca-5(Z),8(Z),11(Z),14(Z)-tetraenoic acid ethyl ester, as an oil.

| | MeOH | |
|---|---|---|
| U.V. | λmax 225 nm | |
| | (ε 7079) | |
| I.R. | (CHCl$_3$) | 1030, 1440, 1580, 1730, 3000 cm$^{-1}$ |
| N.M.R. | (CdCl$_3$) | 1.26 (t, 3H COOCH$_2$CH$_3$) |
| | | 1.73 (m, 2H) |
| | | 2.08 (t, 2H) |
| | | 2.3 (t, 2H) |
| | | 2.8 (s, 6H) |
| | | 3.58 (d, 2H) |
| | | 4.11 (m, 2H COOCH$_2$CH$_3$) |
| | | 5.13–5.66 (m, 8H) |
| | | 7.13–7.5 (m, 5H) |
| M.S. | | 402 (MH$_4$$^+$). |

B. A solution of 601.3 mg (1.56 mmol) of 16-phenylthiohexadeca-5(Z),8(Z),11(Z),14(Z)-tetraenoic acid ethyl ester in 10 ml of 90% aqueous methanol was treated with 10 ml of 0.5N sodium hydroxide solution. The reaction mixture was stirred an additional 12 hours at room temperature.

The solvent was then evaporated in vacuo and the residue diluted with 10 ml of water, acidified with saturated solution of oxalic acid and extracted with methylene chloride (3×30 ml). The combined organic extracts were dried over sodium sulfate and evaporated in vacuo. Purification of the residue by column chromatography on 20 g of silica gel, using methylene chloride as eluant, afforded 16-phenylthiohexadeca-5(Z),8(Z),11(Z),14(Z)-tetraenoic acid, as an oil.

| | MeOH | |
|---|---|---|
| U.V. | λmax 255 nm | |
| | (ε 6607) | |
| I.R. | (CHCl$_3$) | 1240, 1440, 1580, 1710, 2960 cm$^{-1}$ |
| N.M.R. | (CdCl$_3$) | 1.73 (m, 2H) |
| | | 2.1 (t, 2H) |
| | | 2.36 (t, 2H) |
| | | 2.8 (s, 6H) |
| | | 3.6 (d, 2H) |
| | | 5.15–5.66 (m, 8H) |
| | | 7.13–7.5 (m, 5H) |
| | | 8.5 (s broad, 1H COOH) |
| M.S. | | 374 (MH$_4$$^+$). |

The product was stored in dry ice.

EXAMPLE 11

16-(p-methylthiophenoxy)hexadeca-5,8,11,14-tetraynoic acid

A. 27.15 ml (13.75 g, 0.103 mol) of a 3.8N solution of ethylmagnesium bromide in ether was added dropwise under argon to a cold solution of 15.3 g (0.085 mol) of 3-(p-methylthiophenoxy)-1-propyne in 80 ml of anhydrous tetrahydrofuran, at such a rate to maintain the temperature at −10° C. The resulting mixture was stirred for 1 hour and then treated with 677.2 mg of cuprous cyanide. After stirring 20 minutes more, a solution of 10.8 g (0.0687 mol) of 1-bromo-2,5-hexadiyne in 25 ml of anhydrous tetrahydrofuran was added dropwise, maintaining the temperature between 0°–5° C. The reaction mixture was stirred at room temperature for 3 additional hours, and then poured into 150 ml of 1N sulfuric acid and ice. After extraction with ether (3×150 ml) the combined organic extracts were concentrated in vacuo to a small volume, and washed several times with EDTA and then with water, dried over sodium sulfate and evaporated. The crude material was purified by column chromatography on 200 g of silica gel, using hexane:ethyl acetate (95:5) as eluant, and the product crystallized from methylene-chloride-hexane, to yield 9-(p-methylthiophenoxy)-1,4,7-nonatriyne, as an oil. The product was stored in dry ice.

B. 12.03 ml (6.077 g, 0.0455 mol) of 3.8N ethylmagnesium bromide in ether was added dropwise to a solution of 9.65 g (0.0379 mol) of 9-(p-methylthiophenoxy)-1,4,7-nonatriyne in 80 ml of anhydrous tetrahydrofuran. The temperature was maintained at −10° C. The reaction mixture was stirred for 1 hour further at 0° C., allowed to warm to room temperature, and then 374 mg of cuprous cyanide were added. The mixture was stirred for 20 additional minutes, heated to 40° C. and then treated with 13.83 g (49.38 mmol) of 7-iodo-5-heptynoic acid ethyl ester in 30 ml of anhydrous tetrahydrofuran. The resulting mixture was stirred for 3 additional hours at 40° C., then poured on to 300 ml of 1N sulfuric acid and ice. After extraction with ether (3×150 ml), the combined extract was concentrated to a small volume and washed several times with Versene solution and water, dried and evaporated in vacuo. The crude material was purified by column chromatography on 125 g of silica gel, using hexane:ethyl acetate (95:5)

as eluant, to obtain 16-(p-methylthiophenoxy)-hexadeca-5,8,11,14-tetraynoic acid ethyl ester, as an oil. The product was stored in dry ice.

| | MeOH | |
|---|---|---|
| U.V. | λmax 230, 258 nm | |
| | (ε 5623, 6761) | |
| I.R. | (CHCl₃) | 1015, 1320, 1495, 1600, 1725, 2930, 2000 cm⁻¹ |
| N.M.R. | (CdCl₃) | 1.23 (t, 3H COOCH₂CH₃) |
| | | 1.76 (m, 2H) |
| | | 2.23 (t, 2H) |
| | | 2.43 (m, 2H) |
| | | 3.13 (s, 6H) |
| | | 4.1 (m, 2H COOCH₂CH₃) |
| | | 4.63 (s, 2H) |
| | | 6.86 (d, 2H) |
| | | 7.26 (d, 2H) |
| M.S. | | 424 (MNH₄⁺). |

C. 1.7 g of 16-(p-methylthiophenoxy)hexadeca-5,8,11,14-tetraynoic acid ethyl ester was mixed with 168 ml of the pH 6.7 buffer solution prepared in accordance with Example 1. The mixture was vigorously stirred and 16.24 g of Sigma Lipase, Type VII, from Candida cylindracea were added, stirring was continued for 18 hours at room temperature; the reaction mixture was then transferred to a separatory funnel with 200 ml ethyl acetate and acidified with saturated solution of oxalic acid. The organic layer was separated and the aqueous layer extracted with ethyl acetate. The combined organic extract was dried over sodium sulfate and the solvent removed under vacuo. The residue was purified by TLC on silica gel with a Chromatotron using hexane-ethyl acetate (60:40) as the eluant, to yield 16-(p-methylthiophenoxy)hexadeca-5,8,11,14-tetraynoic acid, which was recrystallized from methylene chloride-hexane. M.P. 87°-88° C. (dec).

EXAMPLE 12

16-(p-methylthiophenoxy)hexadeca-5(Z),8(Z),11(Z),14(Z)-tetraenoic acid

A. A solution of 2 g (4.926 mmol) of 16-(p-methylthiophenoxy)hexadeca-5,8,11,14-tetraynoic acid ethyl ester in 80 ml of a 1:1 mixture of methanol:ethyl acetate was hydrogenated at room temperature in the presence of 1 g of pre-reduced Lindlar's catalyst and 0.242 ml of quinoline, until the calculated amount of hydrogen was consumed (615 ml) (585 mm). The catalyst was separated by filtration through Celite and the filtrate evaporated in vacuo. Purification of the residue by silica gel column chromatography (15 g), using hexane:ethyl acetate (98:2) as eluant, afforded 16-(p-methylthiophenoxy)hexadeca-5(Z),8(Z),11(Z),14(Z)-tetraenoic acid ethyl ester, as an oil.

| | MeOH | |
|---|---|---|
| U.V. | λmax 231.5, 257.5 nm | |
| | (ε 9120, 10720) | |
| I.R. | (CHCl₃) | 1020, 1490, 1600, 1725, 2930, 3010 cm⁻¹ |
| N.M.R. | (CdCl₃) | 1.23 (t, 3H COOCH₂CH₃) |
| | | 1.71 (m, 2H) |
| | | 2.05 (t, 2H) |
| | | 2.3 (t, 2H) |
| | | 2.43 (s, 3H S—CH₃) |
| | | 2.83 (t, 6H) |
| | | 4.1 (m, 2H COOCH₂CH₃) |
| | | 4.56 (d, 2H) |
| | | 5.13-5.8 (m, 8H) |
| | | 6.73-7.4 (m, 5H) |
| M.S. | | 414 (M⁺). |

The product was stored in dry ice.

B. 7.7 ml of a 0.5N sodium hydroxide solution was added to a solution of 400 mg of 16-(p-methylthiophenoxy)hexadeca-5(Z),8(Z),11(Z),14(Z)-tetraenoic acid ethyl ester in 15 ml of 80% aqueous methanol and the resulting reaction mixture was stirred at room temperature for 28 hours. Then the solvent was removed in vacuo and the residue was diluted with 10 ml of water, acidified with saturated solution of oxalic acid and extracted with methylene chloride (2×50 ml). The combined organic extracts were dried over sodium sulfate and evaporated in vacuo. The residue was purified by TLC on silica gel with a Chromatotron using hexane:ethyl acetate (70:30) as the eluant, thus obtaining 16-(p-methylthiophenoxy)hexadeca-5(Z),8(Z),11(Z),14(Z)-tetraenoic acid, as an oil.

| | MeOH | |
|---|---|---|
| U.V. | λmax 231, 258 nm | |
| | (ε 8710, 10000) | |
| I.R. | (CHCl₃) | 1240, 1490, 1600, 1710, 3000 cm⁻¹ |
| N.M.R. | (CdCl₃) | 1.66 (m, 2H) |
| | | 2.06 (t, 2H) |
| | | 2.26 (t, 2H) |
| | | 2.43 (s, 3H S—CH₃) |
| | | 2.83 (m, 6H) |
| | | 4.56 (d, 2H) |
| | | 5.1-5.86 (m, 8H) |
| | | 6.66-8.1 (m, 5H) |
| M.S. | | 386 (M⁺). |

The product was stored in dry ice.

EXAMPLE 13

16-[(p-methylsulfonyl)phenoxy]hexadeca-5,8,11,14-tetraynoic acid

A solution of 2.1 g (5.17 mmol) of 16-(p-methylthiophenoxy)hexadeca-5,8,11,14-tetraynoic acid ethyl ester in 10 ml of tetrahydrofuran and 60 ml of methanol was cooled to 0° C. and 9.6 ml (7.74 mmol) of 49.5% aqueous potassium hydrogen persulfate solution was added. The reaction mixture was stirred 90 minutes at room temperature and then the solvent removed under reduced pressure. The residue was diluted with 60 ml of water and extracted with methylene chloride (2×100 ml). The combined extracts were dried over sodium sulfate and the solvents evaporated in vacuo. Purification of the residue by column chromatography on 30 g of silica gel, using hexane:ethyl acetate (70:30) as eluant, produced 16-[(p-methylsulfonyl)-phenoxy]hexa-deca-5,8,11,14-tetraynoic acid ethyl ester, as an oil.

| | MeOH | |
|---|---|---|
| U.V. | λmax 238, 265 nm | |
| | (ε 15490, 2291) | |
| I.R. | (CHCl₃) | 1100, 1320, 1600, 1730, 2440, 2970 cm⁻¹ |
| N.M.R. | (CdCl₃) | 1.25 (t, 3H COOCH₂CH₃) |
| | | 1.85 (m, 2H) |
| | | 2.33 (t, 2H) |
| | | 2.4 (t, 2H) |
| | | 3.03 (s, 3H SO₂—CH₃) |
| | | 3.13 (s, 6H) |
| | | 4.11 (m, 2H COOCH₂CH₃) |
| | | 4.75 (s, 2H) |
| | | 7.08 (d, 2H) |
| | | 7.86 (d, 2H) |

| M.S. | 456 (MNH$_4^+$). |
| --- | --- |

The product was stored in dry ice.

A solution of 1.69 g (3.8 mmol) of 16-[(p-methylsulfonyl)-phenoxy]hexa-deca-5,8,11,14-tetraynoic acid ethyl ester in 25 ml of tetrahydrofuran and 157 ml of the buffer solution (pH 6.7) of Example 1 was sonicated for 10 minutes, then 14.97 g of Sigma Lipase Type VII, from Candida cylindracea was added thereto and the mixture sonicated for 5 additional hours. Then an additional 70 ml of the buffer solution and an additional 7 g of Lipase were additionally added, the stirring resumed for 16 hours further. The mixture was then acidified with saturated aqueous oxalic acid solution and extracted with ethyl acetate (3×300 ml). The organic extracts were dried and the solvents evaporated in vacuo. Purification of the residue by TLC on silica gel with a Chromatotron using ethyl acetate as the eluant afforded 16-[(p-methylsulfonyl)phenoxy]hexadeca-5,8,11,14-tetraynoic acid, which was recrystallized from methylene chloride-hexane. M.P. 107°–108° C.

EXAMPLE 14

16-[(p-methylsulfonyl)phenoxy]hexadeca-5(Z),8(Z),11(Z),14(Z)-tetraenoic acid

A solution of 400 mg (0.9 mmol) of 16-(p-methylthiophenoxy)hexadeca-5(Z),8(Z),11(Z),14(Z)-tetraenoic acid ethyl ester in 4 ml of tetrahydrofuran and 16 ml of methanol was cooled to 0° C. and 1.79 ml of a 49.5% aqueous solution of aqueous potassium hydrogen persulfate solution was added. The reaction mixture was stirred for 2 hours at room temperature, and the solvent removed under reduced pressure. The residue was diluted with 15 ml of water and extracted with methylene chloride (2×30 ml). The combined extracts were dried and the solvents removed by evaporation. Purification of the residue by thin layer chromatography, using hexane:ethyl acetate (70:30) as the eluant (three developments) yielded 16-[(p-methyl-sulfonyl)phenoxy]hexadeca-5(Z),8(Z),11(Z),14(Z)-tetraenoic acid ethyl ester, as an oil. The product was stored in dry ice.

| | MeOH | |
| --- | --- | --- |
| U.V. | λmax 241, 277 nm | |
| | (ε 18620, 741.3) | |
| I.R. | (CHCl$_3$) | 910, 1150, 1320, 1500, 1600, 1730 2940, 3020 cm$^{-1}$ |
| N.M.R | (CdCl$_3$) | 1.26 (t, 3H COOCH$_2$CH$^3$) |
| | | 1.76 (m, 2H) |
| | | 2.1 (t, 2H) |
| | | 2.33 (t, 2H) |
| | | 2.85 (t, 6H) |
| | | 3.03 (s, 3H SO$_2$—CH$_3$) |
| | | 4.16 (m, 2H COOCH$_2$CH$_3$) |
| | | 4.7 (d, 2H) |
| | | 5.16–6.0 (m, 8H) |
| | | 7.4 (d, 2H) |
| | | 7.93 (d, 2H) |
| M.S. | 446 M$^+$. | |

2.82 ml of 0.5N sodium hydroxide solution were added to a solution of 314.9 mg (0.70 mmol) of 16-[(p-methyl-sulfonyl)phenoxy]hexadeca-5(Z),8(Z),11(Z),14(Z)-tetraenoic acid ethyl ester in 3 ml of tetrahydrofuran and 10 ml of 70% aqueous methanol. The mixture was stirred at room temperature for 5 hours, the solvent removed in vacuo and the residue was diluted with 10 ml of water, acidified with saturated oxalic acid solution and extracted with methylene chloride. The combined extracts were dried over sodium sulfate and evaporated. The crude product was purified by TLC on silica gel with a Chromatotron using ethyl acetate as the eluant, to yield 16-[(p-methylsulfonyl)phenoxy]-hexadeca-5(Z),8(Z),11(Z),14(Z)-tetraenoic acid, as an oil. The product was stored in dry ice.

| | MeOH | |
| --- | --- | --- |
| U.V. | λmax 240.5, 277 nm | |
| | (ε 20890, 776.2) | |
| I.R. | (CHCl$_3$) | 960, 1150, 1320, 1500, 1600, 1710 2960 cm$^{-1}$ |
| N.M.R. | (CdCl$_3$) | 1.75 (m, 2H) |
| | | 2.1 (t, 2H) |
| | | 2.38 (t, 2H) |
| | | 2.86 (t, 6H) |
| | | 3.06 (s, 3H SO$_2$—CH$_3$) |
| | | 4.7 (d, 2H) |
| | | 5.26–5.86 (m, 8H) |
| | | 6.66–8.16 (m, 5H) |
| M.S. | | 400 (M$^+$—H$_2$O). |

EXAMPLE 15

16-[(p-methylsulfinyl)phenoxy]hexadeca-5(Z),8(Z),11(Z),14(Z)-tetraenoic acid

A. A solution of 309 mg of 16-(p-methylthiophenoxy)hexadeca-5(Z),8(Z),11(Z),14(Z)-tetraenoic acid ethyl ester in 4 ml of tetrahydrofuran and 12 ml of methanol was cooled to 0° C., and 0.926 ml of 49.5% aqueous solution of potassium hydrogen persulfate solution was added. The resulting mixture was stirred at 0° C. for 5 minutes and the solvent removed under vacuo. The residue was diluted with 10 ml of water and extracted with methylene chloride (3×15 ml), and the combined extract was dried and the solvent evaporated. Purification of the residue by silica gel column chromatography (10 g), using ethyl acetate-hexane (70:30) as eluant afforded 16-[(p-methylsulfinyl)phenoxy]hexadeca-5(Z),8(Z),11(Z),14(Z)-tetraenoic acid ethyl ester, as an oil. The product was stored in dry ice.

| | MeOH | |
| --- | --- | --- |
| U.V. | λmax 243.5 nm | |
| | (ε 14130) | |
| I.R. | (CHCl$_3$) | 1040, 1250, 1500, 1600, 1730, 3000 cm$^{-1}$ |
| N.M.R. | (CdCl$_3$) | 1.26 (t, 3H COOCH$_2$CH$_3$) |
| | | 1.73 (m, 2H) |
| | | 2.1 (t, 2H) |
| | | 2.33 (t, 2H) |
| | | 3.03 (s, 3H SO—CH$_3$) |
| | | 3.2 (t, 6H) |
| | | 4.13 (m, 2H COOCH$_2$CH$_3$) |
| | | 4.65 (d, 2H) |
| | | 5.2–5.9 (m, 8H) |
| | | 7.05 (d, 2H) |
| | | 7.65 (d, 2H) |
| M.S. | | 430 M$^+$. |

B. Upon hydrolysis of 236.5 mg of 16-[(p-methylsulfinyl)phenoxy]hexadeca-5(Z),8(Z),11(Z),14(Z)-tetraenoic acid ethyl ester by alkaline treatment, in accordance with the method of the preceding Example, there were obtained 163.9 mg (74%) of 16-[(p-methylsulfinyl)phenoxy]hexadeca-5(Z),8(Z),11(Z),14(Z)-tetraenoic acid, as an oil.

| U.V. | MeOH λmax 245 nm (ε 11750) | |
|---|---|---|
| I.R. | (CHCl₃) | 1040, 1090, 1250, 1500, 1600, 1710, 2960 cm⁻¹ |
| N.M.R. | (CdCl₃) | 1.75 (m, 2H) |
| | | 2.1 (t, 2H) |
| | | 2.33 (t, 2H) |
| | | 2.85 (m, 9H) |
| | | 4.65 (d, 2H) |
| | | 5.16–6.0 (m, 8H) |
| | | 6.7 (s, broad, 1H COOH) |
| | | 7.38 (d, 2H) |
| | | 7.65 (d, 2H) |
| M.S. | | 402 M⁺. |

EXAMPLE 16

4-phenoxybut-2-yn-1-ol

A. 104.88 ml (96.69 g, 1.15 mol) of dihydropyran was added dropwise to a solution of 90 g (1.07 mol) of 2-butyn-1,4-diol and 9 g of p-toluenesulfonic acid in 1000 ml of tetrahydrofuran at such a rate to maintain the reaction temperature at 0° C. Thereafter the reaction mixture was stirred for 3 hours at room temperature. It was then neutralized with 10 ml of triethylamine and the solvent removed by evaporation in vacuo. The residue was purified by silica gel column chromatography using hexane:ethyl acetate (80:20) as eluant, to yield 2-butyne-1,4-diol monotetrahydropyranyl ether and 55.33 g (20%) of 2-butyne-1,4-diol bistetrahydropyranyl ether.

B. 5.46 g (0.0217 mol) of pyridinium p-toluenesulfonate was added to a solution of 55.33 g (0.21 mol) of 2-butyne-1,4-diol bistetrahydropyranyl ether in 100 ml of ethanol. The resulting mixture was stirred for 2 hours at 55° C. The solvent was removed under reduced pressure and the residue taken up in methylene chloride, washed with saturated sodium chloride solution, dried over sodium sulfate and the solvent removed by evaporation in vacuo. The crude material thus obtained was purified by silica gel column chromatography (500 g) using hexane:ethyl acetate (80:20) as eluant, to yield of the monotetrahydropyranyl ether of 2-butyne-1,4-diol, as an oil.

C. 10.24 ml (15.15 g, 0.1323 mol) of 2-butyne-1,4-diol monotetrahydropyranyl ether was added dropwise to a solution of 15 g (0.088 mol) of methanesulfonyl chloride and 19.79 ml (14.25 g, 0.141 mol) of triethylamine in 250 ml of anhydrous methylene chloride at such a rate to maintain the reaction temperature at 0° C. The reaction mixture was stirred for 30 minutes further at 0° C. Then the reaction mixture was poured into 200 ml of aqueous saturated sodium bicarbonate solution and extracted with methylene chloride. The combined organic extracts were dried over sodium sulfate and the solvent removed in vacuo, to yield crude 4-tetrahydropyranyloxy-butyn-1-ol methanesulfonate. This crude product was dissolved in 50 ml of acetone and treated with a solution of 40.34 g (0.4636 mol) of lithium bromide in 200 ml of acetone, stirring the reaction mixture at room temperature for 1 hour. The solvent was then evaporated and the residue diluted with water (100 ml) and extracted with methylene chloride, the organic extracts were dried over sodium sulfate and evaporated in vacuo. The crude material was purified by silica gel column chromatography using hexane:ethyl acetate (95:5) as eluant to yield 1-bromobut-2-yn-4-ol-tetrahydropyranyl ether, as an oil.

D. 1.10 g of sodium hydroxide was added to a solution of 2.35 g of phenol in 20 ml of absolute ethanol. The mixture was refluxed until complete dissolution, then 2.92 g of 1-bromobut-2-yn-4-ol tetrahydropyranyl ether was added. The reflux was resumed for 2 additional hours. It was then cooled, poured into water and extracted with ether (3×50 ml). The organic extracts were washed with 20% aqueous sodium hydroxide solution and water, dried over sodium sulfate and evaporated in vacuo. The residue was purified by column chromatography on 50 g of silica gel, using hexane:ethyl acetate (98:2) as eluant, to yield 4-phenoxybut-2-yn-1-ol tetrahydropyranyl ether, as an oil.

E. 1.02 g (0.004 mol) of pyridinium p-toluenesulfonate was added to a solution of 2 g of 4-phenoxy-but-2-yn-1-ol tetrahydropyranyl ether in 20 ml of 96% ethanol. The reaction mixture was stirred for 2 hours at 55° C.; the solvent was then removed in vacuo and the residue diluted with 20 ml of water and extracted with methylene chloride (3×20 ml). The combined extracts were dried over sodium sulfate and the solvent evaporated in vacuo. The residue was purified by column chromatography on 30 g of silica gel, using hexane-ethyl acetate (90:10) as eluant, to yield 4-phenoxy-but-2-yn-1-ol, as an oil.

EXAMPLE 17

10-phenoxydeca-2(Z),5(Z),8(Z)-trien-1-ol

A. 1.432 ml (2.12 g, 0.0185 mol) of methanesulfonyl chloride was added dropwise to a solution of 2 g of 4-phenoxybut-2-yn-1-ol and 2.77 ml of triethylamine in 30 ml of methylene chloride at such a rate to maintain the reaction temperature at 0° C. After addition, the resulting mixture was stirred for 30 minutes at 0° C. Then the reaction mixture was poured into 30 ml of saturated aqueous sodium bicarbonate solution and extracted with methylene chloride. The organic extracts were dried over sodium sulfate and the solvent removed by evaporation in vacuo and thus crude 4-phenoxy-but-2-yn-1-ol methanesulfonate was obtained. The foregoing crude mesylate was dissolved in 15 ml of acetone and treated with a solution of 5.55 g of sodium iodide and 1.049 g of sodium bicarbonate in 30 ml of acetone. The reaction mixture was stirred for 1 hour at room temperature and then the solvent was removed under reduced pressure. The residue was diluted with water (25 ml) and extracted with methylene chloride, (3×30 ml) the organic extracts were dried and the solvent removed by evaporation. The residue was purified by silica gel column chromatography (50 g) using hexane:ethyl acetate (95:5) as eluant, to yield 2.3 g (62%) of 1-iodo-4-phenoxybut-2-yne. The product was stored in the refrigerator.

B. 3.99 ml (2.15 g, 0.016 mol) of a 4.05N solution of ethylmagnesium bromide in ether was added dropwise under argon to a solution of 2.879 (0.0161 mol) of hexa-2,5-diyn-1-ol tetrahydropyranyl ether [D. Van der Steen et al, *Recueil* 82, 1015 (1963)] in 30 ml of tetrahydrofuran maintained at −20° C. After the addition was finished, the reaction mixture was stirred for 2 hours further at −20° C. Then, 52.8 mg (0.53 mmol) of cuprous chloride was added. The mixture was stirred for 20 additional minutes, warmed to room temperature and 2.2 g (0.008 mol) of 1-iodo-4-phenoxybut-2-yne was added. The reaction mixture was then stirred at room temperature for 3 hours, poured into 50 ml of saturated ammonium chloride solution and extracted with ether (3×50 ml). The combined extracts were dried over sodium sulfate and the solvent removed by evaporation in vacuo. The residue was purified by column chromatography on 80 g of silica gel, using hexane:ether (90:10) as eluant thus obtaining the tetrahydropyranyl ether of 10-phenoxydeca-2,5,8-triyn-1-ol, as an oil. This product was stored in dry ice.

C. A solution of 5.23 g (0.01624 mol) of the tetrahydro-pyranyl ether of 10-phenoxydeca-2,5,8-triyn-1-ol in 75 ml of methanol and 75 ml of ethyl acetate was hydrogenated at room temperature and atmospheric pressure (585 mm) in the presence of 784 mg of prereduced Lindlar's catalyst and 0.76 ml of quinoline, until the calculated amount of hydrogen was consumed (1.5 lt). The mixture was filtered through Celite and the filtrate evaporated in vacuo. The residue was purified by silica gel column chromatography (100 g) using hexane:ethyl acetate (98:2) as eluant, thus obtaining of 10-phenoxydeca-2(Z),5(Z),8(Z)-trien-1-ol tetrahydro-pyranyl ether, as an oil. The product was stored in dry ice.

D. 2.21 g (0.0088 mol) of pyridinium p-toluenesulfonate was added to a solution of 2.9 g (0.0088 mol) of 10-phenoxydeca-2(Z),5(Z),8(Z)-trien-1-ol tetrahydro-pyranyl ether in 15 ml of 96% ethanol. The reaction mixture was stirred at 55° C. for an additional 3 hours. The solvent was eliminated under reduced pressure and the residue diluted with water and extracted with methylene chloride (3×20 ml). The combined extracts were dried over sodium sulfate and the solvent removed by evaporation in vacuo. The residue was purified by silica gel column chromatography (40 g) using hexane-ethyl acetate (90:10) as eluant, to yield 1.78 g (82%) of 10-phenoxydeca-2(Z),5(Z),8(Z)-trien-1-ol, as an oil.

EXAMPLE 18

16-phenoxyhexadeca-8(Z),11(Z),14(Z)-trien-5-ynoic acid

A. 0.7 ml (1.055 g, 0.0092 mol) of methanesulfonyl chloride was added dropwise to a solution cooled to 0° C. of 1.5 g (0.006 mol) of 10-phenoxydeca-2(Z),5(Z),8(Z)-trien-1-ol and 1.379 ml (0.993 g, 0.0098 mol) of triethylamine in 20 ml of methylene chloride. The reaction mixture was stirred at 0° C. for 30 minutes, then it was poured into 20 ml of saturated aqueous sodium bicarbonate solution and extracted with methylene chloride. The combined extracts were dried over sodium sulfate and evaporated to dryness in vacuo, to produce the crude methanesulfonate. This crude product was dissolved in 10 ml of acetone and treated with a solution of 2.766 g (0.0184 mol) of sodium iodide and 0.522 g (0.0061 mol) of sodium bicarbonate in 30 ml of acetone. The reaction mixture was stirred for 30 minutes at room temperature and then the solvent was removed under reduced pressure. The residue was diluted with water and extracted with methylene chloride, the organic extracts were dried over sodium sulfate and evaporated in vacuo. The crude material was purified by silica gel column chromatography (40 g) using hexane-ethyl acetate (95:5) as eluant, thus obtaining 1-iodo-10-phenoxydeca-2(Z),5(Z),8(Z)-triene, as an oil. The product was stored in dry ice.

B. 2.56 ml of a 3.79N solution of ethylmagnesium bromide in ether was added dropwise under argon to a stirred solution of 545.72 mg (4.872 mmol) of 5-hexynoic acid in 10 ml of anhydrous tetrahydrofuran. Stirring was continued at room temperature for 1 hour. The reaction mixture was then heated to reflux and treated with 925.5 mg of (4.86 mmol) of cuprous iodide, 34 mg (4.89 mmol) of hydroxylamine hydrochloride and 2 ml of hexamethyl-phosphoramide. The reaction mixture was stirred at reflux temperature for 30 minutes more. Then, 345 mg (0.974 mmol) of 1-iodo-10-phenoxydeca-2(Z),5(Z),8(Z)-triene in 2 ml of tetrahydrofuran, were added and the reflux was resumed for an additional 12 hour period. The mixture was then poured into 25 ml of saturated ammonium chloride solution and extracted with ether (3×30 ml). The combined extracts were dried over sodium sulfate and evaporated. The crude product was conventionally esterified with ethereal diazomethane and purified by thin layer chromatography, using hexane:ethyl acetate (90:10) as eluant, to yield 16-phenoxyhexadeca-8(Z),11(Z),14(Z)-trien-5-ynoic acid methyl ester, as an oil.

| | MeOH | |
|---|---|---|
| U.V. | λmax 271, 277.5 nm | |
| | (ε 1698, 1445) | |
| I.R. | (CHCl$_3$) | 1125, 1245, 1495, 1600, 1730, 2950, 3010 cm$^{-1}$ |
| N.M.R. | (CdCl$_3$) | 1.83 (m, 2H) |
| | | 2.16 (t, 2H) |
| | | 2.43 (t, 2H) |
| | | 2.83 (m, 6H) |
| | | 3.3 (s, 3H COOCH$_3$) |
| | | 4.56 (d, 2H) |
| | | 5.2–5.9 (m, 6H) |
| | | 6.6–7.43 (m, 5H) |
| M.S. | | 370 (MNH$_4^+$). |

C. 53.68 mg (1.27 mmol) of lithium hydroxide was added to a solution of 150 mg (0.426 mmol) of 16-phenoxyhexadeca-8(Z),11(Z),14(Z)-trien-5-ynoic acid methyl ester in 5 ml of dimethoxyethane and 1 ml of water. The reaction mixture was stirred for 3 hours at room temperature, evaporated in vacuo and the residue diluted with 3 ml of water, acidified with saturated solution of oxalic acid and extracted with ethyl acetate (3×15 ml). The extracts were dried and evaporated and the residue purified by TLC on silica gel with a Chromatotron, using hexane:ethyl acetate:acetic acid (70:30:1) as the eluant, to yield 49.1 mg (34%) of 16-phenoxyhexadeca-8(Z),11(Z),14(Z)-trien-5-ynoic acid, as an oil.

| | MeOH | |
|---|---|---|
| U.V. | λmax 271, 277 nm | |
| | (ε 1585, 1349) | |
| I.R. | (CHCl$_3$) | 1245, 1495, 1600, 1710, 2920, 3010 cm$^{-1}$ |
| N.M.R. | (CdCl$_3$) | 1.83 (m, 2H) |
| | | 2.26 (t, 2H) |
| | | 2.5 (t, 2H) |
| | | 2.9 (m, 6H) |
| | | 4.63 (d, 2H) |
| | | 5.23–5.9 (m, 6H) |
| | | 6.66–7.46 (m, 6H) |
| M.S. | | 356 (MNH$_4^+$). |

EXAMPLE 19

1-iodo-10-substituted-phenoxydeca-2(Z),5(Z),8(Z)-trienes 1.46 g of sodium hydroxide was added to a solution of 3.47 g of p-cresol in 20 ml of absolute ethanol. The mixture was refluxed until complete dissolution and 5 g of 1-bromo-but-2-yn-4-ol tetrahydropyranyl ether were added. The reflux was continued for 3 hours, poured into water and extracted with ether (3×50 ml). The combined organic extracts were washed with 20% aqueous sodium hydroxide solution and water, dried and evaporated in vacuo. The residue was purified by column chromatography on 50 g of silica gel, using hexane-ethyl acetate (95:5) as eluant to yield 2.62 g (47%) of 4-(p-methylphenoxy)-but-2-yn-1-ol tetrahydropyranyl ether, as an oil. By repeating the procedures of Example 16, part E, Example 17, parts A through D and Example 18, part A, there were successively obtained:

4-(p-methylphenoxy)but-2-yn-1-ol;
4-(p-methylphenoxy)but-2-yn-1-ol methanesulfonate;
1-iodo-4-(p-methylphenoxy)but-2-yne;
10-(p-methylphenoxy)deca-2,5,8-triyn-1-ol tetrahydropyranyl ether;
10-(p-methylphenoxy)deca-2(Z),5(Z),8(Z)-trien-1-ol tetrahydropyranyl ether;
10-(p-methylphenoxy)deca-2(Z),5(Z),8(Z)-trien-1-ol;
10-(p-methylphenoxy)deca-2(Z),5(Z),8(Z)-trien-1-ol methanesulfonate; and
1-iodo-10-(p-methylphenoxy)deca-2(Z),5(Z),8(Z)-triene.

Likewise, substituting o-cresol and m-methoxyphenol for p-cresol, there were obtained as final products:

1-iodo-10-(o-methylphenoxy)deca-2(Z),5(Z),8(Z)-triene and
1-iodo-10-(m-methoxyphenoxy)deca-2(Z),5(Z),8(Z)-triene, respectively.

EXAMPLE 20

16-(p-methylphenoxy)hexadeca-8(Z),11(Z),14(Z)-trien-5-ynoic acid

A. 3.47 ml (0.291 g, 4.55 mol) of a 1.31N solution of n-butyl lithium was added dropwise under argon to a solution 782.9 mg (4.55 mmol) of 5-hexynoic acid methyl ester in 10 ml of anhydrous tetrahydrofuran, cooled to −70° C. The mixture was stirred for 45 minutes at −70° C. and then 433.5 mg (2.27 mmol) of cuprous iodide was added. The mixture was stirred for 10 minutes at −70° C. and thereafter 837.6 mg (2.27 mmol) of 1-iodo-10-(p-methylphenoxy)deca-2(Z),5(Z),8(Z)-triene dissolved in 3 ml of anhydrous tetrahydrofuran was added. The reaction mixture was stirred for 3 hours at 0° C., poured into 15 ml of water, acidified with saturated solution of oxalic acid and extracted with methylene chloride. The organic extracts were dried and the solvent removed by evaporation. The residue was purified by TLC using hexane:ethyl acetate (95:5) as eluant, (3 developments) to yield of 16-(p-methylphenoxy)hexadeca-8(Z),11(Z),14(Z)-trien-5-ynoic acid methyl ester, as an oil.

| U.V. | MeOH<br>λmax 278, 284.5 nm<br>(ε 1585, 1288) | |
|---|---|---|
| I.R. | (CHCl₃) | 1020, 1240, 1440, 1510, 1600, 1730, 3000 cm⁻¹ |
| N.M.R. | (CdCl₃) | 1.83 (m, 2H) |
| | | 2.21 (m, 5H) |
| | | 2.4 (t, 2H) |
| | | 2.8 (s, 6H) |
| | | 3.66 (s, 3H) |
| | | 4.53 (d, 2H) |
| | | 5.2–5.86 (m, 6H) |
| | | 6.6–7.16 (m, 4H) |

| -continued | |
|---|---|
| M.S. | 366 M⁺. |

The product was stored in dry ice.

B. 3.5 ml of water and 97.5 mg of lithium hydroxide hydrate were added to a solution of 283.3 mg of 16-(p-methylphenoxy)hexadeca-8(Z),11(Z),14(Z)-trien-5-ynoic acid methyl ester in 10 ml of dimethoxyethane. The reaction mixture was stirred for 16 hours at room temperature, the solvent was then evaporated, 10 ml of water were added, acidified with saturated solution of oxalic acid and extracted with methylene chloride. The organic extracts were dried and the solvents removed by evaporation in vacuo. The residue was purified by silica gel column chromatography (10 g) using methylene chloride-methanol (98:2) as eluant, to yield 16-(p-methylphenoxy)hexadeca-8(Z),11(Z),14(Z)-trien-5-ynoic acid, as an oil. The product was stored in dry ice.

| U.V. | MeOH<br>λmax 278, 283 nm<br>(ε 1660, 1380) | |
|---|---|---|
| I.R. | (CHCl₃) | 980, 1245, 1430, 1510, 1615, 1710, 2960 cm⁻¹ |
| N.M.R. | (CdCl₃) | 1.83 (m, 2H) |
| | | 2.23 (m, 5H) |
| | | 2.46 (t, 2H) |
| | | 2.83 (s, 6H) |
| | | 4.53 (d, 2H) |
| | | 5.2–5.83 (m, 6H) |
| | | 6.66–7.16 (m, 4H) |
| | | 8.2 (s broad, 1H COOH) |
| M.S. | 352 M⁺. | |

In a similar manner, starting from 1-iodo-10-(o-methylphenoxy)deca-2(Z),5(Z),8(Z)-triene and 1-iodo-10-(m-methoxyphenoxy)deca-2(Z),5(Z),8(Z)-triene there were respectively obtained:

16-(o-methylphenoxy)hexadeca-8(Z),11(Z),14(Z)-trien-5-ynoic acid and
16-(m-methoxyphenoxy)hexadeca-8(Z),11(Z),14(Z)-trien-5-ynoic acid as final products.

EXAMPLE 21

16-(substituted phenoxy)hexadeca-5,8,11,14-tetraynoic acids

By following the methods of Example 1 but using 7-iodo-5-heptynoic acid ethyl ester as reagent in step B, the phenylpropargyl ethers obtained in Preparation 1 gave as final products the corresponding 16-(substituted phenoxy)hexadeca-5,8,11,14-tetraynoic acids listed below, via their respective ethyl esters:

16-(m-fluorophenoxy)hexadeca-5,8,11,14-tetraynoic acid;
16-(o-bromophenoxy)hexadeca-5,8,11,14-tetraynoic acid;
16-(m-bromophenoxy)hexadeca-5,8,11,14-tetraynoic acid;
16-(p-ethylphenoxy)hexadeca-5,8,11,14-tetraynoic acid;
16-(o-ethoxyphenoxy)hexadeca-5,8,11,14-tetraynoic acid;
16-(m-ethoxyphenoxy)hexadeca-5,8,11,14-tetraynoic acid;
16-(p-butylphenoxy)hexadeca-5,8,11,14-tetraynoic acid;
16-(m-trifluoromethylphenoxy)hexadeca-5,8,11,14-tetraynoic acid;

16-(p-trifluoromethylphenoxy)hexadeca-5,8,11,14-tetraynoic acid;
16-(o-cyanophenoxy)hexadeca-5,8,11,14-tetraynoic acid; and
16-(p-cyanophenoxy)hexadeca-5,8,11,14-tetraynoic acid.

Similarly, when using the known 3-(m-methoxyphenoxy)-1-propyne, 3-(p-methoxyphenoxy)-1-propyne and 3-(o-chlorophenoxy)-1-propyne [I. Iway et al, Chem. Pharm. Bull. 11, 1042 (1963)] as starting materials, there were respectively obtained as final products:
16-(m-methoxyphenoxy)hexadeca-5,8,11,14-tetraynoic acid;
16-(p-methoxyphenoxy)hexadeca-5,8,11,14-tetraynoic acid; and
16-(o-chlorophenoxy)hexadeca-5,8,11,14-tetraynoic acid.

EXAMPLE 22

16-(substituted phenoxy)hexadeca-5(Z),8(Z),11(Z),14(Z)-tetraenoic acids

Example 2 was repeated using as starting materials the ethyl esters of the hexadecatetraynoic acids obtained in the preceeding Example, to produce as final products:
16-(m-fluorophenoxy)hexadeca-5(Z),8(Z),11(Z),14(Z)-tetraenoic acid;
16-(o-bromophenoxy)hexadeca-5(Z),8(Z),11(Z),14(Z)-tetraenoic acid;
16-(m-bromophenoxy)hexadeca-5(Z),8(Z),11(Z),14(Z)-tetraenoic acid;
16-(p-ethylphenoxy)hexadeca-5(Z),8(Z),11(Z),14(Z)-tetraenoic acid;
16-(o-ethoxyphenoxy)hexadeca-5(Z),8(Z),11(Z),14(Z)-tetraenoic acid;
16-(m-ethoxyphenoxy)hexadeca-5(Z),8(Z),11(Z),14(Z)-tetraenoic acid;
16-(p-butylphenoxy)hexadeca-5(Z),8(Z),11(Z),14(Z)-tetraenoic acid;
16-(m-trifluoromethylphenoxy)hexadeca-5(Z),8(Z),11(Z),14(Z)-tetraenoic acid;
16-(p-trifluoromethylphenoxy)hexadeca-5(Z),8(Z),11(Z),14(Z)-tetraenoic acid;
16-(o-cyanophenoxy)hexadeca-5(Z),8(Z),11(Z),14(Z)-tetraenoic acid;
16-(p-cyanophenoxy)hexadeca-5(Z),8(Z),11(Z),14(Z)-tetraenoic acid;
16-(m-methoxyphenoxy)hexadeca-5(Z),8(Z),11(Z),14(Z)-tetraenoic acid;
16-(p-methoxyphenoxy)hexadeca-5(Z),8(Z),11(Z),14(Z)-tetraenoic acid; and
16-(o-chlorophenoxy)hexadeca-5(Z),8(Z),11(Z),14(Z)-tetraenoic acid.

EXAMPLE 23

16-(substituted phenylthio)hexadeca-5,8,11,14-tetraynoic acids

In accordance with the method of Example 9, starting from the phenylpropargyl thioethers obtained in Preparation 3, there were prepared:
16-(o-methylphenylthio)hexadeca-5,8,11,14-tetraynoic acid;
16-(m-methylphenylthio)hexadeca-5,8,11,14-tetraynoic acid;
16-(p-methylphenylthio)hexadeca-5,8,11,14-tetraynoic acid; and
16-(p-methoxyphenylthio)hexadeca-5,8,11,14-tetraynoic acid, respectively, via the corresponding ethyl esters.

EXAMPLE 24

16-(substituted phenylthio)hexadeca-5(Z),8(Z),11(Z),14(Z)-tetraenoic acids

The ethyl esters of tetraynoic acids obtained in Example 23 were hydrogenated in the presence of Lindlar's catalyst and thereafter hydrolyzed by alkaline treatment, in accordance with the methods of Example 10, to produce as final products:
16-(o-methylphenylthio)hexadeca-5(Z),8(Z),11(Z),14(Z)-tetraenoic acid;
16-(m-methylphenylthio)hexadeca-5(Z),8(Z),11(Z),14(Z)-tetraenoic acid;
16-(p-methylphenylthio)hexadeca-5(Z),8(Z),11(Z),14(Z)-tetraenoic acid; and
16-(p-methoxyphenylthio)hexadeca-5(Z),8(Z),11(Z),14(Z)-tetraenoic acid, respectively.

EXAMPLE 25

16-(substituted phenoxy)hexadeca-8(Z),11(Z),14(Z)-trien-5-ynoic acids

By following the methods of Example 16, parts D and E, but substituting
m-fluorophenol,
p-chlorophenol,
o-bromophenol,
p-ethylphenol,
o-methoxyphenol,
m-ethoxyphenol,
p-butylphenol,
p-trifluoromethylphenol and
m-cyanophenol for phenol,
there were obtained:
4-(m-fluorophenoxy)but-2-yn-1-ol;
4-(p-chlorophenoxy)but-2-yn-1-ol;
4-(o-bromophenoxy)but-2-yn-1-ol;
4-(p-ethylphenoxy)but-2-yn-1-ol;
4-(o-methoxyphenoxy)but-2-yn-1-ol;
4-(m-ethoxyphenoxy)but-2-yn-1-ol;
4-(p-butylphenoxy)but-2-yn-1-ol;
4-(p-trifluoromethylphenoxy)but-2-yn-1-ol; and
4-(m-cyanophenoxy)but-2-yn-1-ol, respectively, via the corresponding tetrahydropyranyl ethers.

The above-mentioned compounds were submitted to the procedures described in Examples 17 and 18, thus obtaining as final products:
16-(m-fluorophenoxy)hexadeca-8(Z),11(Z),14(Z)-trien-5-ynoic acid;
16-(p-chlorophenoxy)hexadeca-8(Z),11(Z),14(Z)-trien-5-ynoic acid;
16-(p-ethylphenoxy)hexadeca-8(Z),11(Z),14(Z)-trien-5-ynoic acid;
16-(o-methoxyphenoxy)hexadeca-8(Z),11(Z),14(Z)-trien-5-ynoic acid;
16-(m-ethoxyphenoxy)hexadeca-8(Z),11(Z),14(Z)-trien-5-ynoic acid;
16-(p-butylphenoxy)hexadeca-8(Z),11(Z),14(Z)-trien-5-ynoic acid;
16-(p-trifluoromethylphenoxy)hexadeca-8(Z),11(Z),14(Z)-trien-5-ynoic acid; and
16-(m-cyanophenoxy)hexadeca-8(Z),11(Z),14(Z)-trien-5-ynoic acid, respectively, which were purified through the corresponding methyl esters.

EXAMPLE 26

16-phenylthiohexadeca-8(Z),11(Z),14(Z)-trien-5-ynoic acids

A stirred solution of sodium ethoxide in ethanol, obtained from 1.3 g of sodium and 50 ml of absolute ethanol was treated dropwise with 5.5 g (0.05 mol) of thiophenol in 15 ml of absolute ethanol. The reaction mixture was refluxed for 1 hour and then treated with 5.84 g (0.025 mol) of 1-bromobut-2-yn-4-ol tetrahydropyranyl ether, refluxing the mixture for 2 additional hours. It was then cooled, poured into water and extracted with methylene chloride. The organic extract was washed with water, dried and evaporated to dryness in vacuo. The residue was purified by silica gel column chromatography, to produce 4-phenylthiobut-2-yn-1-ol tetrahydropyranyl ether, as an oil. Upon hydrolysis of the ether group with pyridinium p-toluenesulfonate in ethanol, in accordance with the method of Example 16, part E, there was obtained 4-phenylthiobut-2-yn-1-ol.

Similarly, substituting o-thiocresol, m-thiocresol and 4-mercaptoanisol for thiophenol, there were obtained:
4-(o-methylphenylthio)but-2-yn-1-ol;
4-(m-methylphenylthio)but-2-yn-1-ol; and
4-(p-methoxyphenylthio)but-2-yn-1-ol.

The foregoing compounds were then submitted to the reactions described in Examples 17 and 18 to produce as final products:
16-phenylthiohexadeca-8(Z),11(Z),14(Z)-trien-5-ynoic acid;
16-(o-methylphenylthio)hexadeca-8(Z),11(Z),14(Z)-trien-5-ynoic acid;
16-(m-methylphenylthio)hexadeca-8(Z),11(Z),14(Z)-trien-5-ynoic acid; and
16-(p-methoxyphenylthio)hexadeca-8(Z),11(Z),14(Z)-trien-5-ynoic acid, respectively.

EXAMPLE 27

1 ml of ethereal diazomethane was added to a solution of 20 mg of 16-phenylthiohexadeca-5(Z),8(Z),11(Z),14(Z)-tetraenoic acid in 5 ml of ether. The reaction mixture was maintained at room temperature for 10 minutes. The solvent and excess reagent were removed under vacuum, and the residue purified by TLC to produce the methyl ester of 16-phenylthiohexadeca-5(Z),8(Z),11(Z),14(Z)-tetraenoic acid.

In a similar manner,
16(p-methylthiophenoxy)hexadeca-5,8,11,14-tetraynoic acid,
16[(p-methylsulfonyl)phenoxy]hexadeca-5(Z),8(Z),11(Z),14(Z)-tetraenoic acid,
16-[(p-methylsulfinyl)phenoxy]hexadeca-5(Z),8(Z),11(Z),14(Z)-tetraenoic acid and the compounds obtained in Examples 21, 22, 23 and 24 were converted into the corresponding methyl esters.

Likewise, substituting diazopropane for diazomethane in the above-described procedure, the corresponding propyl esters were prepared.

EXAMPLE 28

1.0 molar equivalent of a 0.1N solution of sodium bicarbonate was added to a solution of 100 mg of 16-phenoxyhexadeca-5,8,11,14-tetraynoic acid in 10 ml of methanol. The mixture was stirred at room temperature for 1 hour. The solvent was then removed under reduced pressure, to give the sodium salt of 16-phenoxyhexadeca-5,8,11,14-tetraynoic acid.

By employing 1.0 molar equivalents of potassium bicarbonate (in the form of a 0.1N solution) in place of sodium bicarbonate in the above procedure the potassium salt of 16-phenoxy-hexadeca-5,8,11,14-tetraynoic acid was obtained.

Similarly, the sodium and potassium salts of the tetraynoic, tetraenoic and 8,11,14-trien-5-ynoic acids obtained in the previous Examples can be prepared. Representative compounds are:
sodium salt of 16-(p-methylphenoxy)hexadeca-5,8,11,14-tetraynoic acid;
sodium salt of 16-(m-chlorophenoxy)hexadeca-5,8,11,14-tetraynoic acid;
sodium salt of 16-phenylthiohexadeca-5,8,11,14-tetraynoic acid;
sodium salt of 16-(m-methylphenoxy)hexadeca-5(Z),8(Z),11(Z),14(Z)-tetraenoic acid;
potassium salt of 16-(p-methylsulfonylphenoxy)-hexadeca-5(Z),8(Z),11(Z),14(Z)-tetraenoic acid;
potassium salt of 16-(m-fluorophenoxy)hexadeca-5(Z),8(Z),11(Z),14(Z)-tetraenoic acid;
potassium salt of 16-(o-methylthiophenoxy)hexadeca-5(Z),8(Z),11(Z),14(Z)-tetraenoic acid;
sodium salt of 16-(p-methoxyphenylthio)hexadeca-5(Z),8(Z),11(Z),14(Z)-tetraenoic acid;
sodium salt of 16-phenoxyhexadeca-8(Z),11(Z),14(Z)-trien-5-ynoic acid;
sodium salt of 16-(p-methylphenoxy)hexadeca-8(Z),11(Z),14(Z)-trien-5-ynoic acid; and
potassium salt of 16-(o-methoxyphenoxy)hexadeca-8(Z),11(Z),14(Z)-trien-5-ynoic acid.

EXAMPLE 29

A mixture of 2 ml of concentrated ammonium hydroxide solution and 2 ml of methanol was added to a solution of 50 mg of 16-(p-methylphenoxy)-hexadeca-5,8,11,14-tetraynoic acid in 3 ml of methanol. The resulting mixture was stirred for 2 hours at room temperature and then evaporated to dryness in vacuo, to yield the ammonium salt of 16-(p-methylphenoxy)hexadeca-5,8,11,14-tetraynoic acid which was purified by TLC.

By employing 1.1 molar equivalent of trimethylamine, diethylamine and dipropylamine in place of ammonium hydroxide in the above procedure, the corresponding salts of 16-(p-methylphenoxy)hexadeca-5,8,11,14-tetraynoic acid were obtained. In a similar manner, the ammonium, trimethylamine, diethylamine and dipropylamine salts of the other tetraynoic, tetraenoic and 8,11,14-trien-5-ynoic acids of the previous Examples can be prepared.

EXAMPLE 30

A solution of 50 mg of 16-(p-chlorophenoxy)hexadeca-5(Z),8(Z),11(Z),14(Z)-tetraenoic acid in 10 ml of 90% aqueous methanol was treated with 1.0 molar equivalents of procaine and the resultant reaction mixture was stirred at room temperature for 16 hours. It was then evaporated to dryness under reduced pressure, to give the procaine salt of 16-(p-chlorophenoxy)hexadeca-5(Z),8(Z),11(Z),14(Z)-tetraenoic acid.

Similarly, the lysine, caffeine and tromethamine salts of 16-(p-chlorophenoxy)hexadeca-5(Z),8(Z),11(Z),14(Z)-tetraenoic acid, as well as the corresponding salts of 16-(m-methylphenoxy)hexadeca-5,8,11,14-tetraynoic acid;

16-phenylthiohexadeca-5(Z),8(Z),11(Z),14(Z)-tetraenoic acid,

16-[(p-methylsulfinyl)phenoxy]hexadeca-5(Z),8(Z),11(Z),14(Z)-tetraenoic acid, 16-phenoxyhexadeca-8(Z),11(Z),14(Z)-trien-5-ynoic acid and 16-(p-methlphenoxy)hexadeca-8(Z),11(Z),14(Z)-trien-5-ynoic acid were prepared.

EXAMPLE 31

The following example illustrates the preparation of representative pharmaceutical formulations containing an active compound of formula I, e.g., 16-(m-chlorophenoxy)hexadeca-5(Z),8(Z),11(Z),14(Z)-tetraenoic acid.

| I.V. Formulation | |
|---|---|
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

Other compounds of Formula A and the pharmaceutically acceptable salts thereof may be substituted therein.

EXAMPLE 32

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 33

| Ingredients | Quantity per capsule, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 34

TOPICAL FORMULATION

This formulation is a variation of Beeler's Base (See Remington's Pharmaceutical Sciences, 15th Ed., p. 1534)

| Active ingredient | 1 g |
|---|---|
| Cetyl Alcohol | 15 g |
| White Wax | 1 g |
| Propylene Glycol | 10 g |
| Sodium Lauryl Sulfate | 2 g |
| Water | 72 g |

The cetyl alcohol, white wax and active ingredient are heated together at about 65° C. in propylene glycol. The sodium lauryl sulfate and water are mixed together. The two solutions are then mixed together, and stirred well. The well mixed solution is removed from the heat and mixed to the point of congealing.

EXAMPLE 35

| Ingredients | Quantity per capsule, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 36

| Ingredients | Quantity per tablet, mgs. |
|---|---|
| Active ingredient | 150 |
| lactose | 92 |

The above ingredients are mixed and introduced into a hard-shell gelatin tablet.

EXAMPLE 37

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 38

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 39

Conversion of 16-(p-methylphenoxy)hexadeca-5,8,11,14-tetraynoic acid into the Sodium Salt Sodium methoxide (82 mg) is added to a solution of 16-(p-methylphenoxy)-hexadeca-5,8,11,14-tetraynoic acid (500 mg) in methanol (5 ml). The solution is then evaporated to dryness to afford 16-(p-methylphenoxy)-hexadeca-5,8,11,14-tetraynoic acid sodium salt.

In a similar manner, all compounds of formula (A), may be converted to salts such as potassium, lithium, ammonium, calcium, magnesium, ferrous, zinc, copper, manganous, aluminum, ferric, manganic salts and the like.

EXAMPLE 40

Conversion of 16-(p-methylphenoxy)hexadeca-5,8,11,14-tetraynoic acid Sodium Salt into 16-(p-methylphenoxy)hexadeca-5,8,11,14-tetraynoic acid benzoic acid A two-fold stoichiometric excess of N-hydrochloric acid is added to a solution of 16-(p-methylphenoxy)-hexadeca-5,8,11,14-tetraynoic acid sodium salt in water. The solution is then extracted with ether, and the extract is dried and evaporated to afford 2-(heptadeca-5'(Z),8'(Z),11'(Z)-trien-2'-ynylthio)benzoic acid.

EXAMPLE 41

Assay for Inhibition of Lipoxygenase Activity In Human Polymorphonuclear Leukocytes (PMNs)

Experimental Procedures

1. Preparation of the cells:

The PMNs are prepared from 200-300 ml of heparinized blood of healthy donors not receiving any medication for at least 7 days using Ficol-Hypaque gradients. In general, PMNs are greater than 90% pure and their viability was assessed by dye-exclusion to be better than 95%. The cells are suspended in phosphate buffered saline containing 1.0 mM $CaCl_2$ (PH 7.4) and 0.1% ovalbumin, and used within 30 minutes.

2. Lipoxygenase Assay:

Incubations are carried out at 37° C. for 5 minutes in a total volume of 0.2 ml arachidonic acid 1-$C^{14}$ ($1\times10^{-4}$M unless otherwise indicated, and approximately 300,000 cpm) was added to a suspension of cells (ca $5\times10^6$) to initiate the reaction. Prior to the addition of above substrate, the test substances are added to the cells at appropriate concentrations and pre-incubated at 37° C. for 5 minutes. In general, stock solutions of test substances are prepared in ethanol (or other appropriate solvents) and diluted with either incubation-buffer or water. The final concentration of ethanol in the incubation did not exceed 1%. Boiled enzyme blanks and controls containing no test compound are always included. The incubations are terminated by the addition of 0.6 ml of methanol, vortexed and kept on ice for 30 minutes.

1.6 ml of deionized water is added, vortexed, centrifuged, the supernatants decanted and kept in the freezer overnight. Separation of arachidonic acid and lipoxygenase products are carried out using "Baker" disposable $C^{-18}$ extraction columns (1 ml capacity). The columns are prewashed with MeOH (2.0 ml) followed by deionized water (2 ml). After most of the solvent is removed, 2.0 ml of the supernatant is applied to the extraction columns and the solvent is allowed to flow through. The columns are then washed with 5 ml of deionized water and the eluate is discarded. The columns are then eluted with 6.0 ml of a solvent mixture (acetonitrite:H$_2$O:acetic acid in the proportion 50:50:0.1) which recovers all the arachidonic acid metabolites including 5-HETE and LTB$_4$ with very little of arachidonic acid (AA) being eluted (less than 2-3% of incubated counts). The columns are then eluted with 2.0 ml of methanol (forced through by N$_2$) which elutes all of the unreacted substrate AA. The eluates are collected in scintillation vials and 1.0 ml aliquot from each of the two fractions are counted for radioactivity in a Packard liquid scintillation counter. From the radioactivity data thus obtained percent yields of total lipoxygenase products in blanks, controls and drug containing tubes are calculated as well as percent inhibition by the test compounds.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings.

What is claimed is:

1. A compound of the formula

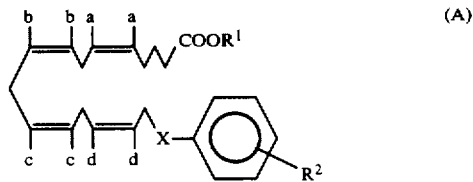

(A)

wherein:

X is O or S;

R$^1$ is hydrogen, lower alkyl or a pharmaceutically acceptable cation;

R$^2$ is hydrogen, lower alkyl, lower alkoxy, halo, cyano, trifluoromethyl, lower alkylthio, lower alkylsulfinyl or lower alkylsulfonyl, provided that when X is S R$^2$ cannot be alkylsulfinyl or alkylsulfonyl; and each pair of a—a, b—b, c—c, and d—d are independently hydrogens or a covalent bond.

2. The compound of claim 1 wherein each pair of a—a, b—b, c—c, and d—d represents a covalent bond.

3. The compound of claim 2 wherein X is O.

4. The compound of claim 3 wherein R$^1$ is hydrogen, methyl, ethyl, sodium cation, potassium cation, or ammonium cation, and R$^2$ is hydrogen, methyl, ethyl, methoxy, ethoxy, chloro, or methyl—S(O)$_n$, where n is 0, 1 or 2.

5. The compound of claim 4 wherein R$^1$ is hydrogen and R$^2$ is p-methyl namely 16-(p-methylphenoxy)-hexadeca-5,8,11,14-tetraynoic acid.

6. The compound of claim 4 wherein R$^1$ is hydrogen and R$^2$ is o-methyl namely 16-(o-methylphenoxy)-hexadeca-5,8,11,14-tetraynoic acid.

7. The compound of claim 4 wherein R$^1$ is hydrogen and R$^2$ is m-methyl namely 16-(m-methylphenoxy)-hexadeca-5,8,11,14-tetraynoic acid.

8. The compound of claim 4 wherein R$^1$ is hydrogen and R$^2$ is hydrogen namely 16-phenoxyhexadeca-5,8,11,14-tetraynoic acid.

9. The compound of claim 4 wherein R$^1$ is hydrogen and R$^2$ is m-chlorp, namely 16-(m-chlorophenoxy)-hexadeca-5,8,11,14-tetraynoic acid.

10. The compound of claim 4 wherein R$^1$ is hydrogen and R$^2$ is p-methylthio, namely, 16-(p-methylthiophenoxy)-hexadeca-5,8,11,14-tetraynoic acid.

11. The compound of claim 4 wherein $R^1$ is hydrogen and $R^2$ is p-methylsulfonyl namely, 16-[(p-methylsulfonyl)phenoxy]-hexadeca-5,8,11,14-tetraynoic acid.

12. The compound of claim 2 wherein X is S.

13. The compound of claim 12 wherein $R^1$ is hydrogen, methyl, ethyl, sodium cation, potassium cation, or ammonium cation, and $R^2$ is hydrogen, methyl, ethyl, methoxy, ethoxy, chloro, or methyl—$S(O)_n$, where n is 0, 1 or 2.

14. The compound of claim 13 wherein $R^1$ is hydrogen and $R^2$ is hydrogen namely 16-phenylthio-hexadeca-5,8,11,14-tetraynoic acid.

15. The compound of claim 1 wherein each pair of a—a, b—b, c—c, and d—d are all hydrogens.

16. The compound of claim 15 wherein X is O.

17. The compound of claim 16 wherein $R^1$ is hydrogen, methyl, ethyl, sodium cation, potassium cation, or ammonium cation, and $R^2$ is hydrogen, methyl, ethyl, methoxy, ethoxy, chloro, or methyl—$S(O)_n$, where n is 0, 1 or 2.

18. The compound of claim 17 wherein $R^1$ is hydrogen and $R^2$ is m-methyl namely 16-(m-methylphenoxy)-hexadeca-5(Z),8(Z),11(Z),14(Z)-tetraenoic acid.

19. The compound of claim 17 wherein $R^1$ is hydrogen and $R^2$ is p-methylsulfinyl namely 16-[(p-methylsulfinyl)phenoxy]hexadeca-5(Z),8(Z),11(Z),14(Z)-tetraenoic acid.

20. The compound of claim 17 wherein $R^1$ is hydrogen and $R^2$ is hydrogen, namely 16-phenoxy-hexadeca-5(Z),8(Z),11(Z),14(Z)-tetraenoic acid.

21. The compound of claim 17 wherein $R^1$ is hydrogen and $R^2$ is p-methyl, namely 16-[(paramethyl)phenoxy]hexadeca-5(Z),8(Z),11(Z),14(Z)-tetraenoic acid.

22. The compound of claim 17 wherein $R^1$ is hydrogen and $R^2$ is m-chloro, namely 16-[(m-chloro)phenoxy]-hexadeca-5(Z),8(Z),11(Z),14(Z)-tetraenoic acid.

23. The compound of claim 17 wherein $R^1$ is hydrogen and $R^2$ is p-methylthio, namely 16-[(p-methylthio)phenoxy]-hexadeca-5(Z),8(Z),11(Z),14(Z)-tetraenoic acid.

24. The compound of claim 17 wherein $R^1$ is hydrogen and $R^2$ is p-sulfonylmethyl, namely 16-[(p-sulfonylmethyl)phenoxy]-hexadeca-5(Z),8(Z),11(Z),14(Z)-tetraenoic acid.

25. The compound of claim 1 wherein the pair a—a is a covalent bond and, b—b, c—c, and d—d are all hydrogen atoms.

26. The compound of claim 25 wherein X is O.

27. The compound of claim 26 wherein $R^1$ is hydrogen, methyl, ethyl, sodium cation, potassium cation, or ammonium cation, and $R^2$ is hydrogen, methyl, ethyl, methoxy, ethoxy, chloro, or methyl—$S(O)_n$, where n is 0, 1 or 2.

28. The compound of claim 27 wherein $R^1$ is hydrogen and $R^2$ is hydrogen namely 16-phenoxyhexadeca-8(Z),11(Z),14(Z)-trien-5-ynoic acid.

29. The compound of claim 27 wherein $R^1$ is hydrogen and $R^2$ is p-methyl namely 16-(p-methylphenoxy)-hexadeca-8(Z),11(Z),14(Z)-trien-5-ynoic acid.

30. A method of treating a mammal having a disease state characterized by overproduction of the products of lipoxygenase metabolism of arachidonic acid, which method comprises administering a therapeutically effective amount of a compound of claim 1 to the mammal.

31. The method of claim 30 wherein said disease state is an inflammatory disease.

32. The method of claim 30 wherein said disease state is rheumatoid arthritis.

33. The method of claim 30 wherein said disease state is asthma.

34. The method of claim 30 wherein said disease state is thrombosis.

35. A pharmaceutical formulation comprising a therapeutically effective amount of a compound of claim 1 and a pharmaceutically acceptable excipient.

* * * * *